(12) United States Patent
Kraus et al.

(10) Patent No.: US 8,247,572 B2
(45) Date of Patent: Aug. 21, 2012

(54) FACILITATED TRANSPORT OF BISPHOSPHONATES BY VITAMIN C

(75) Inventors: Virginia Byers Kraus, Hillsborough, NC (US); Amy Lynn McNulty, Bahama, NC (US); Eric John Toone, Durham, NC (US)

(73) Assignee: Duke University, Durham, NC (US)

( * ) Notice: Subject to any disclaimer, the term of this patent is extended or adjusted under 35 U.S.C. 154(b) by 1002 days.

(21) Appl. No.: 11/911,679

(22) PCT Filed: Apr. 21, 2006

(86) PCT No.: PCT/US2006/015051
§ 371 (c)(1),
(2), (4) Date: Jul. 22, 2008

(87) PCT Pub. No.: WO2006/116057
PCT Pub. Date: Nov. 2, 2006

(65) Prior Publication Data
US 2008/0305039 A1    Dec. 11, 2008

Related U.S. Application Data

(60) Provisional application No. 60/673,527, filed on Apr. 21, 2005.

(51) Int. Cl.
*A61K 31/445* (2006.01)
*C07D 211/72* (2006.01)
*C07D 411/00* (2006.01)

(52) U.S. Cl. ............... 546/290; 546/281.7; 514/336; 514/345

(58) Field of Classification Search .................. None
See application file for complete search history.

(56) References Cited

U.S. PATENT DOCUMENTS
5,583,122 A    12/1996   Benedict et al.

FOREIGN PATENT DOCUMENTS
WO    WO 02-070499 A3    9/2002
WO    WO 2006-116057 A2    11/2006

OTHER PUBLICATIONS

Silva et al Advances in Prodrug Design in Mini-Reviews in Medicinal Chem 2005, vol. 5, pp. 893-914.*
PCT International Search Report for PCT/US06/15051, Sep. 4, 2007.
Kleine T O and Baumann H J. On the detection of a blood-joint barrier for radiosulfate and [3H]glucosamine in single joints of aging rats. Z Gerontol. (Nov.-Dec. 1991), vol. 24, No. 6, pp. 306-310 (Abstract only).
Meyer J M et al. Anti-resorptive potency alone does not predict the efficacy of bisphosphonates in the rat adjuvant model of rheumatoid arthritis. p. 16. 30th European Symposium on Calcified Tissues—Abstracts (May 2003), pp. 1, 9, printed Apr. 4, 2005. www.ectsoc.org/rome2003/posters1.htm.
McNulty A L et al. Chondrocyte transport and concentration of ascorbic acid is mediated by SVCT2. Biochimica et Biophysica Acta (2005) vol. 1712, pp. 212-221.
McNulty A L et al. Dehydroascorbate transport in human chondrocytes is regulated by hypoxia and is a physiologically relevant source of ascorbic acid in the joint. Arthritis & Rheumatism (Sep. 9, 2005) vol. 52, No. 9, p. 2676-2685.
Manfredini S et al. Design, synthesis and activity of ascorbic acid prodrugs of nipecotic, kynurenic and diclophenamic acids, liable to increase neurotropic activity. J. Med. Chem (2002) vol. 45, No. 3, pp. 559-562.
Füvesi J et al. Comparative study on the effects of kynurenic acid and glucosamine-kynurenic acid. Pharmacology, Biochemistry and Behavior (2004) vol. 77, pp. 95-102.

* cited by examiner

*Primary Examiner* — Janet Andres
*Assistant Examiner* — Heidi Reese
(74) *Attorney, Agent, or Firm* — Myers Bigel Sibley & Sajovec, P.A.

(57) ABSTRACT

Compounds of the formula: are described wherein: $A^1$ is ascorbic acid, dehydroascorbic acid, ascorbyl-2-phosphate, an analog thereof, or a salt thereof; L is a linking group coupled to $A^1$ at the C5 or C6 position thereof; and $B^1$ is an active agent such as an imaging agent or therapeutic agent (e.g. a bisphosphonate), along with pharmaceutically acceptable salts and prodrugs thereof. The compounds are useful for, among other things, improving cartilage uptake of active agents administered for joint diseases such as osteoarthritis and rheumatoid arthritis, and for improving gastrointestinal absorption of bisphosphonates.

16 Claims, 13 Drawing Sheets

FACILITATED TRANSPORT OF BISPHOSPHONATES BY VITAMIN C

CROSS-REFERENCE TO RELATED APPLICATIONS

This application is a national phase application of PCT Application PCT/US2006/015051, filed Apr. 21, 2006, and published in English on Nov. 2, 2006 as International Publication No. WO 2006/116057, and which claims the benefit of U.S. Provisional Application Ser. No. 60/673,527, filed Apr. 21, 2005, the disclosures of which are incorporated herein by reference in their entirety.

FIELD OF THE INVENTION

The present invention concerns compounds, compositions and methods for facilitating transport of active agents such as bisphosphonates into chondrocytes and/or across the gastrointestinal epithelium.

BACKGROUND OF THE INVENTION

Risedronate, a bisphosphonate commercially available as ACTONEL® for the treatment of osteoporosis, has the structure:

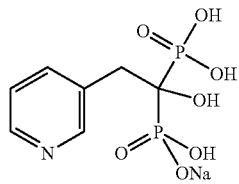

See generally U.S. Pat. Nos. 6,465,443; 6,432,932; 6,165,513; 6,096,342; 6,015,081; 5,994,329; and 5,583,122. A problem with bisphosphonates is their poor bioavailability, and there is a need for new ways to administer bisphosphonate molecules.

SUMMARY OF THE INVENTION

A first aspect of the invention is a compound of the formula:

$$A^1\text{-L-}B^1 \text{ or } A^1\text{-}B^1 \quad (I)$$

wherein:
$A^1$ is ascorbic acid, dehydroascorbic acid, ascorbyl-2-phosphate, an analog thereof, or a salt thereof;
L is a linking group coupled to $A^1$ at the C5 or C6 position thereof; and
$B^1$ is an active agent such as an imaging agent or therapeutic agent (e.g. a bisphosphonate);
or a pharmaceutically acceptable salt or prodrug thereof.

A second aspect of the invention is a composition comprising a compound as described above in a pharmaceutically acceptable carrier.

The present invention also relates to methods of improving cartilage uptake of active agents administered systemically or intra-articularly for joint diseases such as osteoarthritis and rheumatoid arthritis. The method also relates to improving gastrointestinal absorption of bisphosphonates.

The present invention also relates to methods for inhibiting bone resorption or joint tissue resorption or degeneration in a mammal in need thereof, while minimizing the occurrence of or potential for adverse gastrointestinal effects, said method comprising administering to said mammal a pharmaceutically effective amount of an active agent as described herein.

A further aspect of the present invention is a method of treating osteoporosis in a subject in need thereof, comprising administering the subject a treatment-effective amount of an active agent as described herein.

In other embodiments the present invention relates to a method for treating or preventing a condition or disease state in a mammal in need thereof selected from the group consisting of Paget's disease, abnormally increased bone turnover, periodontal disease, tooth loss, bone fractures, metastatic bone disease, hypercalcemia of malignancy, multiple myeloma, and chondrosarcoma, said method comprising administering to said mammal a pharmaceutically effective amount of an active agent as described herein.

A still further aspect of the present invention is the use of an active agent as described above for the preparation of a medicament for the treatment of a disorder as described above.

The present invention is explained in greater detail in the following non-limiting Examples

DETAILED DESCRIPTION OF PREFERRED EMBODIMENTS

Figures 1A, 1B:
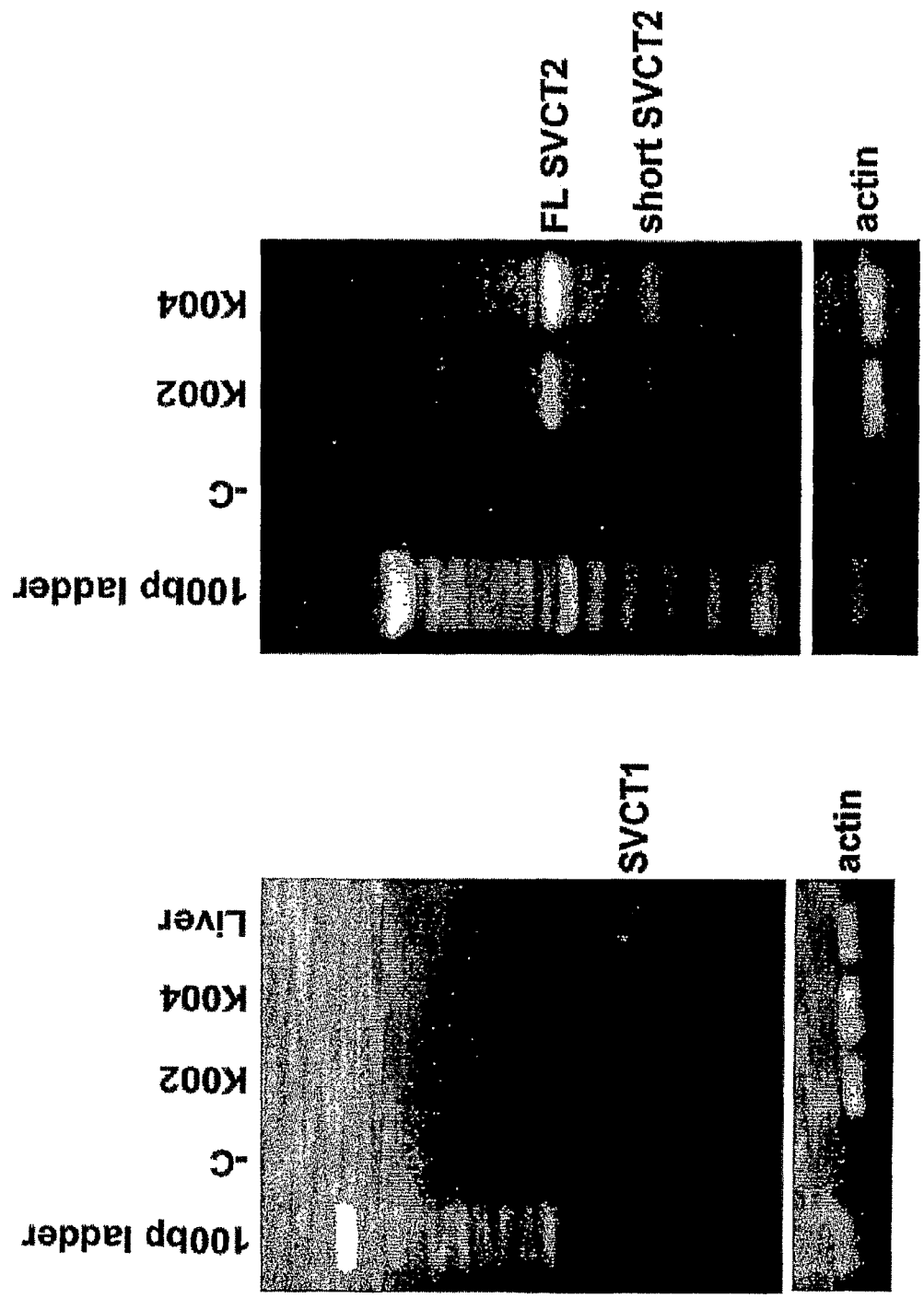
FIG. 1. Chondrocyte expression of SVCT2 but not SVCT1. (A) RT-PCR amplification of SVCT1 (top panel) and actin (bottom panel) from two different lines of passaged primary human chondrocytes (K002 and K004) and human liver. (B) RT-PCR amplification of SVCT2 (top panel) and actin (bottom panel) from two different lines of passaged primary human chondrocytes (K002 and K004). The 646 bp fragment represents the full-length (FL) SVCT2 PCR product and the 301 bp fragment represents the short SVCT2 isoform. The negative control (−C) contained $dH_2O$ instead of cDNA. The 100 bp ladder was used as a size reference.

The term "treat" as used herein refers to any type of treatment that imparts a benefit to a patient afflicted with a disease, including improvement in the condition of the patient (e.g., in one or more symptoms), delay in the progression of the disease, etc.

The term "pharmaceutically acceptable" as used herein means that the compound or composition is suitable for administration to a subject to achieve the treatments described herein, without unduly deleterious side effects in light of the severity of the disease and necessity of the treatment.

Active compounds of the present invention may optionally be administered in conjunction with other compounds useful in the treatment of the disorders or disease states described herein. The other compounds may optionally be administered concurrently. As used herein, the word "concurrently" means sufficiently close in time to produce a combined effect (that is, concurrently may be simultaneously, or it may be two or more events occurring within a short time period before or after each other).

As used herein, the administration of two or more compounds "in combination" means that the two compounds are administered closely enough in time that the presence of one alters the biological effects of the other. The two compounds may be administered simultaneously (i.e., concurrently) or sequentially. Simultaneous administration may be carried out by mixing the compounds prior to administration, or by administering the compounds at the same point in time but at different anatomic sites or using different routes of administration.

The phrases "concurrent administration," "administration in combination," "simultaneous administration" or "administered simultaneously" as used herein, interchangeably mean that the compounds are administered at the same point in time or immediately following one another. In the latter case, the two compounds are administered at times sufficiently close that the results observed are indistinguishable from those achieved when the compounds are administered at the same point in time.

The term "pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response and the like, commensurate with a reasonable risk/benefit ratio, and effective for their intended use, as well as the zwitterionic forms, where possible, of the compounds of the invention. The term "prodrug" refers to compounds that are rapidly transformed in vivo to yield the parent compound of the above formulae, for example, by hydrolysis in blood. A thorough discussion is provided in T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein. See also U.S. Pat. No. 6,680,299 Examples include a prodrug that is metabolized in vivo by a subject to an active drug having an activity of active compounds as described herein, wherein the prodrug is an ester of an alcohol or carboxylic acid group, if such a group is present in the compound; an acetal or ketal of an alcohol group, if such a group is present in the compound; an N-Mannich base or an imine of an amine group, if such a group is present in the compound; or a Schiff base, oxime, acetal, enol ester, oxazolidine, or thiazolidine of a carbonyl group, if such a group is present in the compound, such as described in U.S. Pat. No. 6,680,324 and U.S. Pat. No. 6,680,322.

"Joint disease" as used herein may be any type of joint disease, including but not limited to arthritis of any type (including but not limited to gout, osteoarthritis, and rheumatoid arthritis), joint disease from joint injury (acute and chronic), pseudogout, as well as other forms of joint disease (including any joint such as knee, hip, hand, spine etc.).

The present invention is primarily concerned with the treatment of human subjects, but the invention may also be carried out on animal subjects, particularly mammalian subjects such as mice, rats, dogs, cats, livestock and horses for veterinary purposes, and for drug screening and drug development purposes.

The disclosures of all patent references cited herein are to be incorporated herein by reference in their entirety.

1. Active Compounds.

The methods of the present invention include the administration of compounds of Formula I, while pharmaceutical compositions of the present invention comprise compounds of Formula I. As used herein, a compound of Formula I is as follows:

$$A^1\text{-L-}B^1 \text{ or } A^1\text{-}B^1 \tag{1}$$

wherein:

$A^1$ is ascorbic acid, dehydroascorbic acid (DHA), ascorbyl-2-phosphate, and salt derivatives and analogs thereof;

L is a linking group coupled to said ascorbic acid or analog thereof, preferably at the C5 or C6 position thereof; and $B^1$ is coupled through a linker or directly to $A^1$ and is a active agent such as a bisphosphonate; or a peptide (with anti-inflammatory, anti-degenerative, or anabolic properties); or a glycosaminoglycan such as glucosamine or chondroitin sulfate; or an imaging agent, particularly a radionuclide, such as $^{99}$technetium, $^{99}$technetium-bisphosphonate, or other radioimaging agents, or an imaging agent such as a fluorescently labeled peptide for imaging joint tissues or other fluorescently tagged molecule, or nucleic acid, such as RNA, small interfering RNAs, and oligonucleotides, or intracellular-acting enzyme inhibitors, or intracellular-acting anti-oncolytic agents, or intracellular molecules or their inhibitors involved with arthritis pathogenesis.

or a pharmaceutically acceptable salt or prodrug thereof.

Compounds of Formula I are made in accordance with known techniques or variations thereof which will be apparent to persons skilled in the art in light of the instant disclosure, as discussed further below.

A. Ascorbic acid and analogs. Ascorbic acid, the oxidized derivative, dehydroascorbic acid (DHA), and ascorbyl-2-phosphate (A2P) and their salts and analogs thereof (such as 6-chloro-6-deoxy-L-ascorbic acid, 6-bromo-6-deoxy-L-ascorbic acid, 6-deoxy-6-fluoro-L-ascorbic acid, 6-deoxy-6-iodo-L-ascorbic acid, etc.) are known and described in, for example U.S. Pat. No. 4,043,937 to Kiss and Berg. Additional examples include 6-chloro-6-deoxy-A2P, 6-bromo-6-deoxy-A2P, 6-deoxy-6-fluoro-A2P, 6-deoxy-6-iodo-A2P, etc.). 5-chloro-5-deoxy-L-ascorbic acid/-DHA/-A2P, 5-bromo-5-deoxy-L-ascorbic acid/-DHA/-A2P, 5-deoxy-5-fluoro-L-ascorbic acid/-DHA/-A2P, 5-deoxy-5-iodo-L-ascorbic acid/-DHA/-A2P, etc.

Thus in some embodiments $A^1$ is

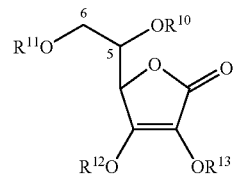

wherein:

one of $R^{10}$ and $R^{11}$ is H, and the other is a covalent link to $B^1$ or L; and $R^{12}$ and $R^{13}$ are each independently selected from the group consisting of H and $PO_3H_2$ (for example: $R^{12}$ and $R^{13}$ are both H; or $R^{12}$ is H and $R^{13}$ is $PO_3H_2$; or $R^{12}$ and $R^{13}$ are both $PO_3H_2$; or $R^{12}$ is $PO_3H_2$ and $R^{13}$ is H); or in some embodiments subject to the proviso that at least one of $R^{12}$ and $R^{13}$ is $PO_3H_2$.

In other embodiments, $A^1$ is

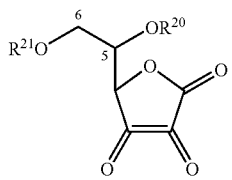

wherein:
one of $R^{20}$ and $R^{21}$ is H, and the other is a covalent link to $B^1$ or L.

B. Bisphosphonates. Bisphosphonates useful as $B^1$ are known and described in, for example, U.S. Pat. Nos. 6,465,443; 6,432,932; 6,165,513; 6,096,342; 6,015,081; 5,994,329; and 5,583,122. Suitable examples of bisphosphonates which may be coupled to linking group L in the present invention include compounds of Formula (II)

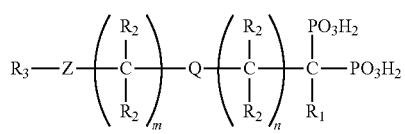

wherein:
Q is oxygen, —$NR^4$—, selenium, —N—, or a single bond;
m+n is an integer from 0 to about 5
Z is a five or six-membered aromatic ring selected from the group consisting of pyridine, pyridazine, pyrimidine, and pyrazine;
$R_1$ is hydrogen, substituted or unsubstituted amino, amido, hydroxy, alkoxy, halogen, carboxylate, substituted or unsubstituted alkyl (saturated or unsaturated) having from 1 to about 6 carbon atoms, substituted or unsubstituted aryl, or substituted or unsubstituted benzyl, except that when n=0 and Q is oxygen, selenium, or —$NR^4$— then $R_1$ is hydrogen, substituted or unsubstituted alkyl (saturated or unsaturated) having from 1 to about 6 carbon atoms, substituted or unsubstituted aryl, or substituted or unsubstituted benzyl, with $R_1$ being hydrogen, chloro, amino, methyl, or hydroxy preferred;
each $R_2$ is, independently, hydrogen, or substituted or unsubstituted alkyl (saturated or unsaturated) having from 1 to about 4 carbon atoms;
$R_3$ is one or more substituents selected from the group consisting of hydrogen, substituted or unsubstituted alkyl (saturated or unsaturated) having from 1 to about 6 carbon atoms, substituted and unsubstituted aryl, substituted and unsubstituted benzyl, hydroxy, halogen, carbonyl, alkoxy, nitro, amido, amino, substituted amino, carboxylate, and combinations thereof, with preferred being hydrogen, methyl, amino, chloro, methoxy, nitro, hydroxy and combinations thereof;
$R_4$ is hydrogen, substituted or unsubstituted alkyl (saturated or unsaturated) having from 1 to about 4 carbon atoms, or acyl (i.e., the amide of the nitrogen),
and for any of the $R_1$, $R_2$, $R_3$, or $R_4$ substituents which are themselves substituted, the substitution on these substituents may be any one or more of the above substituents, preferred being methyl, ethyl, amino, chloro, nitro, methoxy, hydroxy, acetamido, and acetate.

Specific examples of bisphosphonates that may be used to carry out the present invention include but are not limited to alendronate, risedronate, tiludronate, ibandronate, zolendronate, pamidronate, etidronate, and salts and esters thereof.

C. Linking groups. Linking groups L for coupling two separate groups such as $A^1$ and $B^1$ herein are known and described in, for example, U.S. Pat. Nos. 6,872,841; 6,607,741; 6,624,317; 6,593,334; 6,566,393, 6,420,377; and 6,207,673.

Ascorbic acid, dehydroascorbic acid, ascorbyl-2-phosphate, their salts and analogs thereof may be linked via the C5 or C6 position in accordance with known techniques, including but not limited to those described in PCT Application WO 02/070499.

Linking group L is preferably coupled to the aryl group Z of the bisphosphonate such as given in Formula II above, either directly to Z or by coupling to a substituent $R_3$ of Formula II.

For example, the liking group may be an alkylene, alkylenecarbonyl, carbonylalkylene, a carbonyl group, or maleimide as follows:

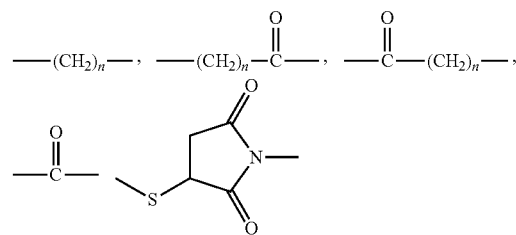

where n is 0 (i.e., a direct covalent linkage) or is from 1 to 6. Such alkylene groups may be saturated or unsaturated, and may be substituted 1, 2, 3, or 4 times with C1-C4 alkyl, halo, phenyl, or halo-substituted phenyl. Examples are as follows:

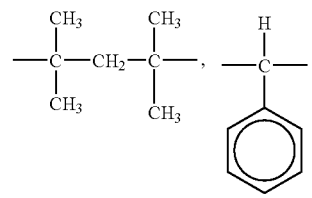

A phenyl or phenylene group, or two or more linked phenylene groups, may be provided as the linking group, which phenylene group may optionally be substituted 1, 2, 3 or four times with a halogen or alkyl group. Examples are as follows:

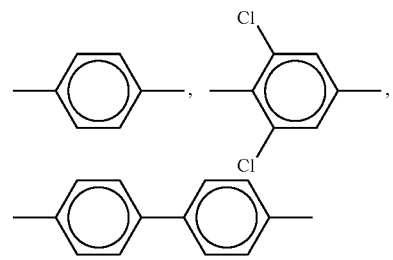

A substituted or unsubstituted phenylene group may be joined at either or both ends with a substituted or unsubstituted alkylene, alkylenecarbonyl, carbonylalkylene, or carbonyl group as described above to provide a linking group. Examples are as follows:

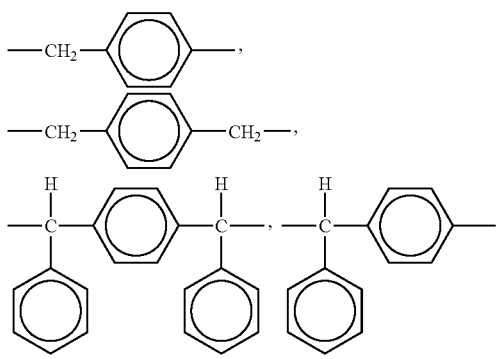

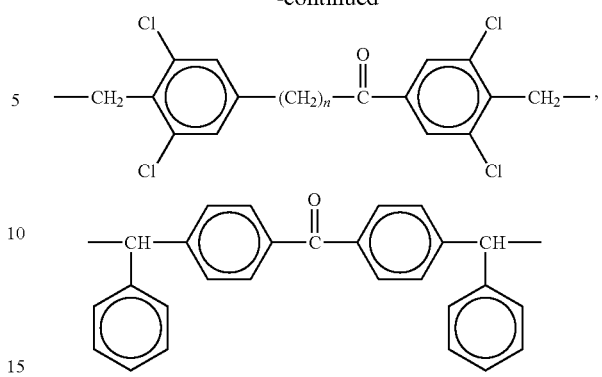

A substituted or unsubstituted alkylene, alkylenecarbonyl, carbonylalkylene, or carbonyl group as described above may joined at either or both ends to a substituted or unsubstituted phenylene group as described above to provide a linking group. Examples are as follows:

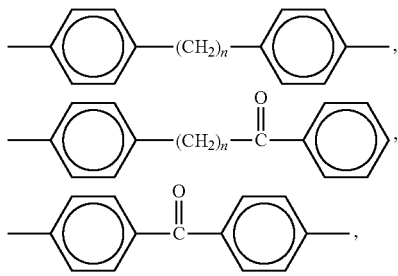

where "n" is as defined above. Such compounds may be further substituted at either or both ends by a substituted or unsubstituted alkylene, alkylenecarbonyl, carbonylalkylene, or carbonyl group, as described above, to provide still further linking groups. Examples are as follows:

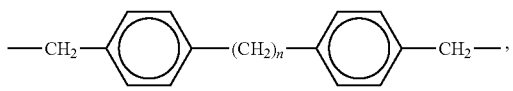

where "n" is as defined above.

Linking groups as described above can be coupled one to the other (e.g., a maleimide group to an alkyl chain) to produce still other linking linking groups useful for carrying out the present invention.

In all examples above but not limited to these examples, L can include an ester linkage at the site of attachment to ascorbic acid, dehydroascorbic acid, or ascorbyl-2-phosphate, or their salts and analogs thereof to facilitate hydrolysis, in vivo or in vitro, of the conjugate molecule.

D. Example compounds. Compounds illustrative of the compounds of Formula (I) above include, but are not limited to:

(a)

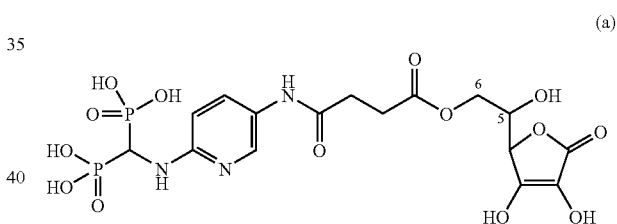

(BPAA), and pharmaceutically acceptable salts and prodrugs thereof; as well as:

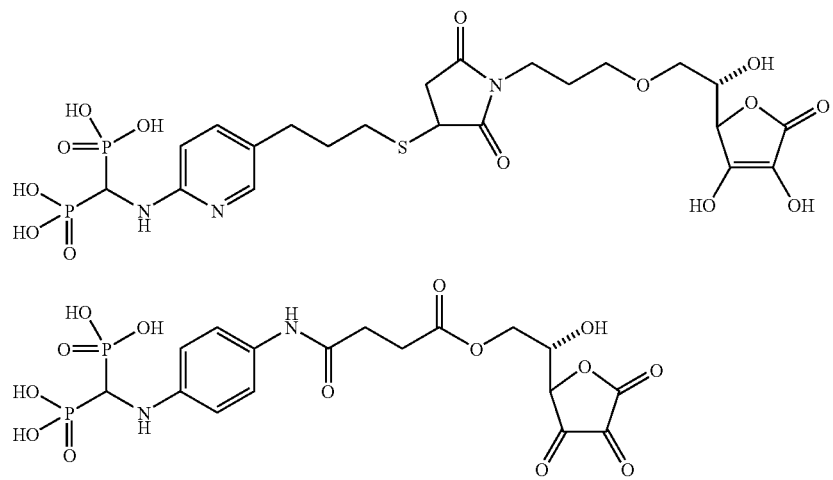

-continued

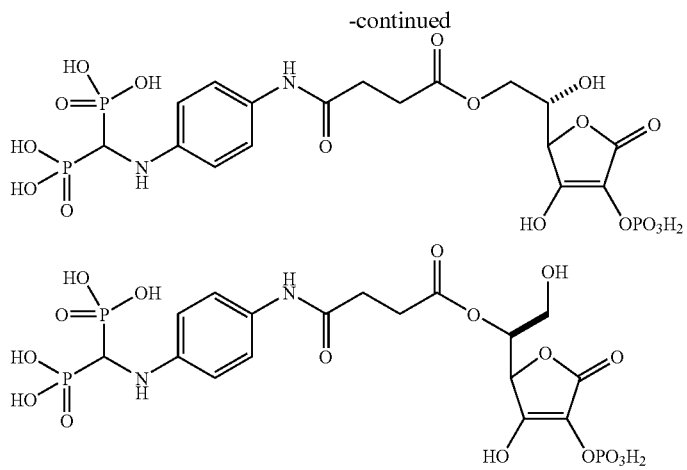

alternate stereoisomers of the foregoing, and pharmaceutically acceptable salts and prodrugs thereof.

The active compounds disclosed herein can, as noted above, be prepared in the form of their pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

2. Pharmaceutical Formulations.

The active compounds described above may be formulated for administration in a pharmaceutical carrier in accordance with known techniques. See, e.g., Remington, *The Science And Practice of Pharmacy* ($9^{th}$ Ed. 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well known techniques of pharmacy comprising admixing the components, optionally including one or more accessory ingredients.

The formulations of the invention include those suitable for oral, rectal, topical, buccal (e.g., sub-lingual), vaginal, parenteral (e.g., intra-articular, subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the active compound, which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising a compound of Formula (I), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bis\tris buffer (pH 6) or ethanol/water and contain from 0.1 to 0.2M active ingredient.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the compounds disclosed herein or salts thereof, may be lyophilized to produce a lyophilizate which may be reconstituted with a pharmaceutically acceptable carrier, such as water, to regenerate a liposomal suspension.

Other pharmaceutical compositions may be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidyl cholines, and lecithin.

In addition to compounds of formula (I) or their salts, the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

3. Dosage and Routes of Administration.

As noted above, the present invention provides pharmaceutical formulations comprising the active compounds (including the pharmaceutically acceptable salts thereof), in pharmaceutically acceptable carriers for oral, rectal, topical, buccal, parenteral, intramuscular, intradermal, intravenous, and transdermal administration.

In some embodiments, administration by intraarticular injection is preferred.

The therapeutically effective dosage of any specific compound, the use of which is in the scope of present invention, will vary somewhat from compound to compound, and patient to patient, and will depend upon the condition of the patient and the route of delivery. As a general proposition, a dosage from about 0.01 or 0.1 to about 50 or 100 mg/kg will have therapeutic efficacy, with all weights being calculated based upon the weight of the active compound, including the cases where a salt is employed.

The present invention is explained in greater detail in the following non-limiting Examples.

EXAMPLE 1

The following compounds and disorders are additional examples of how the present invention may be carried out:

Bisphosphonate derivatives: Bisphosphonates have been shown to have chondroprotective effects. These agents are poorly absorbed and concentrations to cartilage are suboptimal. We will couple these agents to AA/DHA/ or A2P (at the 5 or 6 positions) to improve gastrointestinal absorption and chondrocyte uptake. These studies were enabled using an analog of risedronate conjugated to AA, 6-O-{N-[6-[(bisphosphonomethyl)amino]pyridin-3-yl]}succinyl-L-ascorbic acid. This and other structures to be used in these claims are shown below.

Peptides (with anti-inflammatory, anti-degenerative, or anabolic properties): Peptides are difficult to transport across the cellular membrane. We will couple AA/DHA/ or A2P (at the 5 or 6 positions) to facilitate concentrative transport of specific peptides. One example of an anti-inflammatory peptide is a small apoE-mimetic peptide derived from the receptor binding region of the ApoE holo protein (apoE-(133-149)). This peptide suppresses inflammatory responses in mice after lipopolysaccharide administration (Lynch, JBC 278:48529, 2003. The 17-amino acid sequence is LRBRLASHLRKLRKRLL. This is an example of the sort of peptide we will link to AA/DHA/or A2P (directly or via a linker, such as maleimide).

Glycosaminoglycan such as glucosamine or chondroitin sulfate: Glycosaminoglycans (GAGs) have both analgesic and chondroprotective effects. GAGs, such as chondroitin sulfate, are poorly absorbed through the gastrointestinal system. GAGs, such as glucosamine, achieve only low concentrations in joint fluid when administered orally. These may act as building blocks for cartilage proteoglycan synthesis and may also inhibit glycosylphosphatidylinositol (GPI) anchor formation, among other possible intracellular mechanisms of action. We plan to conjugate AA/DHA/ or A2P to these and other GAGs to gastrointestinal absorption and chondrocyte uptake.

Imaging agent such as $^{99}$technetium, $^{99}$technetium-bisphosphonate, or other radioimaging agents: Technetium-99m is the most widely used radionuclide for medical indications. Moreover, Technetium-99m (99 mTc) is readily coupled to carrier molecules. The trend in nuclear medicine is to develop tailor made or receptor-specific carrier molecules which target specific organs or disease states and carry 99 mTc or other radionuclides to the sites in the body that are to be imaged. We will couple Tc99m to AA/DHA or A2P to target uptake of the radiolabel to cells with the AA/DHA transporters. The safety of high intracellular Tc99m is demonstrated by Tc99m-sestamibi used in cardiac imaging. The Tc99m-AA/DHA or A2P will have specific applicability in imaging cartilage. Tc99m-methylene disphosphonate (a Tc99m-bisphosphonate compound commonly used to image bone) will also be coupled to AA/DHA or A2P to enhance cartilage uptake over bone uptake.

Imaging agent such as a fluorescently labeled peptide for imaging joint tissues, or other fluorescently tagged molecule: Only live cells will transport and concentrate AA. A method of visualizing viable tissue will be to conjugate a fluorescent molecule, such as fluorescein isothiocyanate (FITC), to the 5 or 6 positions (with or without a linker) of AA/DHA/ or A2P. This will allow concentration and visualization of FITC within live cells.

Nucleic acid, such as RNA, small interfering RNAs, and oligonucleotides: Nucleic acids are difficult to transport across the eukaryotic cell membranes. We will couple AA/DHA/or A2P (at the 5 or 6 positions) to facilitate concentrative transport of specific nucleic acids. Examples of nucleic acids include small interfering RNAs (siRNAs). The following sequences have specifically been shown to suppress the expression of GLUT1: GGAGUUCUACAACCA-GAC, GGUGAUCGAGGAGUUCUAC, and GGAUU-UUAACAAAAGCAAG and GLUT3: GGAGAAUGCUAAGCAGAUC and GGAUACAUGUGC-CGAAUGU (McNulty, Arthritis & Rheumatism, 2005). These are examples of the sort of nucleic acids we will link to AA/DHA/or A2P (directly or via a linker, such as maleimide).

Intracellular-acting enzyme inhibitors: P38 MAP kinase is an example of an enzyme that is a key regulator of chondrocyte gene expression. Inhibition of p38 MAP kinase delays hypertrophic differentiation, including reduced expression of collagen type X, matrix metalloproteinase 13, bone sialoprotein (Stanton, Biochem. J. 378 Part I: 53, 2004). We will couple AA/DHA/or A2P (at the 5 or 6 positions) to a p38 MAP kinase inhibitor, such as PD16936, to enhance the concentration of this enzyme inhibitor intracellularly. This is an example of the sort of enzyme inhibitor that we will link to AA/DHA/or A2P (directly or via a linker, such as maleimide).

Intracellular-acting anti-oncolytic agents: Chondrosarcoma is a common form of bone cancer that affects cartilage cells. It is the second most common type of bone cancer after osteosarcoma. Surgery, radiation, and chemotherapy are all used to treat chondrosarcomas. Exposure of the cancer site to a chemotherapeutic agent conjugated to AA/DHA/ or A2P will be used to specifically target and concentrate chemotherapeutic agents within cancer cells. Examples of chemotherapeutic agents used to treat chondrosarcoma include the following: adriamycin, ifosfamide, cisplatin, and methotrexate (Dickey, JBJS 86: 2412, 2004). These are examples of the sort of chemotherapeutic agents that we will link to AA/DHA/ or A2P (directly or via a linker, such as maleimide).

Intracellular molecules or their inhibitors involved with arthritis pathogenesis: One example of an intracellular molecule that is critical in the pathogenesis of arthritis is NFkB. NFkB is involved in the influx of inflammatory cells into the synovium, the activation of inflammatory cells in the synovium, and the degradation of cartilage and bone. Compounds that could downregulate NFkB would be useful treatments for arthritis. Pyrrolidine dithiocarbamate (PDTC), bay 11-7085, and MG132 are inhibitors of NFkB (Lawrence, Nature Medicine 7(12): 1292, 2001) that will be linked to AA/DHA/ or A2P (directly or via a linker, such as maleimide).

A second example of an intracellular molecule that is critically related to the inflammation associated with arthritis is cyclooxygenase. Non-steroidal anti-inflammatory agents (NSAIDs) and more specific NSAIDs, the COX-2 inhibitors, block prostaglandin production associated with arthritis. NSAIDs are associated with significant gastrointestinal and cardiovascular toxicity. A method of limiting toxicity is to deliver the agent locally and to facilitate cellular uptake. We will conjugate a AA/DHA or A2P to a NSAID (these include ibuprofen) or a COX-2 inhibitor (these include celecoxib) for topical or intra-articular administration to achieve highly localized intracellular concentrations in joint tissues at sites of arthritis.

EXAMPLE 2

Chondrocyte Transport and Concentration of Ascorbic Acid is Mediated by SVCT2

We have reported that cartilage may be a storage site for AA, having shown that cartilage concentrations of AA are 3-8 times higher than levels in synovial fluid [23]. This is consistent with the essential role of AA in type II collagen extracellular matrix synthesis. However, it was not determined whether the AA was concentrated inside the chondrocytes or trapped in the cartilage extracellular matrix. Therefore, in this study we have examined the ability of chondrocytes to concentrate AA. We have also evaluated the mechanism of transport of the reduced form of AA in primary human chondrocytes to discern the physiologically relevant pathways of AA transport in cartilage. Our data represent the first evidence that chondrocytes concentrate AA and that this concentrative transport is mediated by SVCT2.

Materials and Methods

Chondrocyte Isolation and Cell Culture. Articular cartilage was obtained from human knee surgical waste tissues at the time of knee replacement surgery (n=7). Primary human chondrocytes were isolated from cartilage specimens, which were harvested from non-lesioned areas. For each specimen, the cartilage was minced and the chondrocytes isolated by enzymatic digestion, similar to methods published previously [24]. Cells were given fresh media every three days and passaged upon confluence, approximately once every 10 days. The cells were cultured for no longer than eight passages. Every experimental treatment was performed at least one time in duplicate within the first seven passages. We verified that cells within the first seven passages consistently expressed aggrecan and collagen II. Due to limited availability of primary chondrocytes and to further confirm the results obtained from earlier passages, subsequent competition and inhibition experiments were performed in passage eight cells. No difference was observed between earlier and later passages in either expression or activity of the SVCTs.

Explant Isolation and Culture. Cartilage explants were isolated from human knee articular cartilage surgical waste tissues at the time of knee replacement surgery (n=5). Cartilage was harvested from non-lesioned areas, using a 2 mm diameter micro dissecting trephine (Biomedical Research Instruments, Rockville, Md.). A group of five cartilage plugs was pooled to constitute one sample. Each sample was paired with a corresponding sample from the same specimen and the same sites. The cartilage plugs were weighed and then transferred to a 24-well plate, containing 1 ml wash media (described in the chondrocyte isolation procedure). The cartilage plugs were incubated in 1 ml DMEM/F12 (Gibco, Grand Island, N.Y.) with 10% FCS (Gibco) and no AA for 48 hours at 37° C./5% $CO_2$, prior to the procedures below.

Ascorbic Acid Concentration in Cartilage Explants. AA transport by live cartilage explants was compared with uptake by dead explants to differentiate the potential for active transport from passive interaction of AA with the cartilage extracellular matrix.

Live/Dead Generation. The cartilage explants were washed with PBS and half of the samples were transferred to 1.5 ml centrifuge tubes with a drop of PBS. The tubes were frozen in liquid nitrogen for three minutes and thawed at 37° C. for five minutes. This freeze/thaw procedure was performed for a total of three cycles. The dead explants were transferred back to the 24-well plates.

Cell Viability Assay. Cartilage plugs were harvested as described above and then washed three times in transport buffer (see AA Transport Assay in Isolated Primary Human Chondrocytes). Explants were cut in half and cell viability was assessed with the Live-Dead assay (Molecular Probes, Eugene, Oreg.), according to the manufacturer's protocol. The explants were then viewed with the Zeiss LSM 510 (Carl Zeiss Inc., Thornwood, N.Y.) to verify the live or dead state of the chondrocytes within the explants.

Explant Ascorbic Acid Transport Assay. Explants were washed three times in transport buffer (see AA Transport Assay in Isolated Primary Human Chondrocytes). A stock solution of L-[$^{14}$C]-ascorbic acid (L-$^{14}$C-Asc, 4 mCi/mmol, NEN, Boston, Mass.) in 0.4 mM DL-homocysteine (Sigma, Saint Louis, Mo.) was diluted to a final concentration of 50 µM L-$^{14}$C-Asc. Each sample was incubated with 1 ml of 50 µM L-$^{14}$C-Asc for 21-22 hours at 37° C./5% $CO_2$. The samples were then washed four times with ice-cold PBS to remove extracellular L-$^{14}$C-Asc. Samples were processed to isolate the cells from the matrix fraction (see Intracellular versus Extracellular AA) or counted for radioactivity by transferring the whole explants to glass scintillation vials and solubilizing the samples overnight at room temperature in 0.5 ml Solulene 350 (Perkin Elmer Life and Analytical Services, Boston, Mass.). Hionic Fluor scintillation fluid (5 ml, Perkin Elmer Life and Analytical Services) was added, and radioactivity was counted in the live and dead explants, using a scintillation counter.

Intracellular versus Extracellular Ascorbic Acid. Explant isolation, explant treatments, and the explant AA transport assay (through the PBS wash step) were performed, followed by the chondrocyte isolation procedure described above. After the cell fraction was isolated from the matrix, the cells were washed, then 15 µl of the cells were counted on a hemacytometer, in order to determine the total number of cells in the cell fraction. The remaining cell fraction was lysed in 300 µl Puregene Cell Lysis Solution (Gentra Systems, Minneapolis, Minn.) and scintillation counting was performed in Uniscint BD (National Diagnostics, Atlanta, Ga.). The total fmol of L-$^{14}$C-Asc inside the chondrocytes was calculated using the total dpm (disintegrations per minute) of L-$^{14}$C-Asc measured and the specific activity of the radiolabel. The average fmol of L-$^{14}$C-Asc inside each chondrocyte was calculated by dividing the total fmol L-$^{14}$C-Asc in the cell lysate by the total number of cells in the lysate. The concentration inside each chondrocyte was calculated, using the data for the fmol L-$^{14}$C-Asc per cell and the average human chondrocyte (from non-eroded articular cartilage) total cell volume of 550 µm$^3$ (mathematically equivalent to $1.346 \times 10^{-12}$ L) (P. G. Bush, A. C. Hall, The volume and morphology of chondrocytes within non-degenerate and degenerate human articular cartilage, Osteo. Cart. 11 (2003) 242-51). Bush and Hall have shown that the volume of chondrocytes in non-degenerate human cartilage increases from the superficial to the deep zones of cartilage, ranging from 396 µm$^3$ to 590 µm$^3$ (P. G. Bush, A. C. Hall, The volume and morphology of chondrocytes within non-degenerate and degenerate human articular cartilage, Osteo. Cart. 11 (2003) 242-51). Our full thickness cartilage explants contained cells from the superficial, middle, and deep zones of cartilage and thus our results depict the possible range of intracellular AA concentrations, depending on the location of the chondrocyte in the cartilage extracellular matrix. The fold concentration inside the chondrocytes was determined by comparing the intracellular concentration of L-$^{14}$C-Asc to the concentration in the media (50 µM).

Ascorbic Acid Transport Assay in Isolated Primary Human Chondrocytes. AA transport was measured using a modified version of the uptake assay published by Wilson and Dixon (J. X. Wilson, S. J. Dixon, High-Affinity Sodium-Dependent Uptake of Ascorbic Acid by Rat Osteoblasts, J. Mem. Biol. 111 (1989) 83-91). Primary human chondrocytes were seeded at a density of $4.5 \times 10^5$ cells/well on a 6-well plate (or $2.25 \times 10^5$ cells/well on a 12-well plate for the kinetic experiments). Prior to the transport assay, cells were plated for 48 hours in DMEM/F12, containing 10% FCS but no AA. Cells were washed in transport buffer containing: 134 mM NaCl, 5.4 mM KCl, 1.8 mM $CaCl_2$, 0.8 mM $MgSO_4$, 10 mM D-glucose, 20 mM HEPES, pH 7.3 with NaOH. AA uptake was assessed by incubating the chondrocytes in transport buffer containing 189 µM L-$^{14}$C-Asc. Immediately before use, the L-$^{14}$C-Asc was solubilized in 0.4 mM DL-homocysteine (Sigma) to prevent AA oxidation. The standard AA transport assay conditions were 37° C./5% $CO_2$ for 10 minutes. AA uptake was terminated by washing the cells four-times in ice-cold PBS. The cells were lysed with Puregene Cell Lysis Solution (Gentra Systems) and scintillation counting was performed in Uniscint BD (National Diagnostics). The total pmol of L-$^{14}$C-Asc transported was calculated using the total dpm of L-$^{14}$C-Asc transported and the specific activity of the radiolabel.

We performed AA transport assays under various conditions designed to augment or inhibit the function of the AA transporters, including variations of the following: time; +/−134 mM Na$^+$; +/−10 mM D-glucose; temperature (4° C. or 37° C.); 100 µM Cytochalasin B (Sigma), 100 µM Cytochalasin E (Sigma), and 100 µM Sulfinpyrazone (Sigma); 2 mM unlabeled L-ascorbic acid (L-Asc, Sigma), L-DHA, D-isoascorbic acid (D-Asc, Aldrich), Na L-ascorbate (Na L-Asc, Sigma), and Na D-isoascorbate (Na D-Asc, Aldrich); increasing concentrations of unlabeled L-Asc; and 0-500 µM L-$^{14}$C-Asc. In experiments with sodium free transport buffer, iso-osmotic concentrations of LiCl were substituted for NaCl. Sulfinpyrazone is an anion transport inhibitor (R. T. Franceschi, J. X. et al, Requirement for Na(+)-dependent ascorbic acid transport in osteoblast function, Am. J. Physiol. 268 (1995) C1430-9), while cytochalasin B inhibits transport via the GLUTs (R. Deves, R. M. Krupka, Cytochalasin B and the kinetics of inhibition of biological transport: a case of asymmetric binding to the glucose carrier, Biochim. Biophys. Acta 510 (1978) 339-48) and also inhibits actin polymerization. Cytochalasin E has no known inhibitory effects on transport mechanisms but also inhibits actin polymerization and thus is a control for the actin effects of cytochalasin B. The properties of the AA forms used in these experiments were discussed in detail previously (A. G. Clark, et al, The effects of ascorbic acid on cartilage metabolism in guinea pig articular cartilage explants, Matrix Biol. 21 (2002) 175-184). Stock solutions of DHA were generated immediately before use by incubating 2 mM L-Asc in 0.4 mM homocysteine with an AA oxidase spatula (Roche Diagnostics, Mannheim, Germany) for 15 minutes, stirring at room temperature. Detailed HPLC analyses (see below) of the DHA generated from L-Asc, using AA oxidase, revealed that on average, the oxidation process resulted in conversion of all of the L-Asc to DHA (41+/−6%) or metabolites of DHA (59%). Thus, the "2 mM" DHA stock solutions contained approximately 0.82 mM DHA.

High Performance Liquid Chromatography (PLC). The integrity of the L-$^{14}$C-Asc stocks utilized in these experiments was determined by measuring the proportion of AA and DHA by HPLC. AA was measured with an electrochemical detector (EC), using the method of Lee et al. (W. Lee, et al, Ascorbic acid in lymphocytes: cell preparation and liquid-chromatographic assay, Clin. Chem. 28 (1982) 2165-9). The amount of AA oxidation to DHA in the stocks and samples was determined by reducing the DHA to AA, as previously described (W. A. Behrens and R. Madere, A highly sensitive high-performance liquid chromatography method for the estimation of ascorbic and dehydroascorbic acid in tissues, biological fluids, and foods, Anal. Biochem. 165 (1987) 102-7).

RNA Isolation. Monolayer cells were grown to confluency on 35 mm plates and the cells were lysed, using 1 ml of Trizol reagent (Gibco). The RNA extraction procedure was carried out according to the manufacturer's protocol through the phase separation step. The aqueous phase was transferred to a new tube and 10 μg tRNA (Sigma) was added. Then 0.5 ml isopropanol was added and the sample was frozen overnight at −80° C. The RNA was pelleted at 13,000 rpm for 20 minutes at 4° C., the liquid phase was discarded, and the pellet was air dried. The RNA was then processed according to the manufacturer's protocol for the Qiagen RNeasy kit (Qiagen, Valencia, Calif.).

RT-PCR. Total RNA was reverse transcribed into complementary DNA (cDNA), using Superscript II Reverse Transcriptase (Gibco) and random hexamer primers. Multiple Choice human liver cDNA (Origene, Rockville, Md.) was used as a positive control for SVCT1 expression. Intron spanning primers were designed for actin (5'GACTACCTCATGAAGATCCT3' and 5'ATCCACATCTGCTGGAAGGT3'), SVCT1 (5'GCCCCTGAACACCTCTCATAT3' and 5'ATGGCCAGCATGATAGGAAA3'), and SVCT2 (5'AAGCACTGGGGCATTGCCAT3' and 5'GTAATTCCCAAAACTCCAAT3'), corresponding to the human sequences available in Genbank. The following PCR primers were also generated to distinguish the full length SVCT2 transcript from the short form (splice variant) of SVCT2, identified recently by Lutsenko et al. (E. A. Lutsenko et al, A human sodium-dependent vitamin C transporter 2 isoform acts as a dominant-negative inhibitor of ascorbic acid transport. [erratum appears in Mol Cell Biol. 2004 July; 24(14): 6537], Mol. Cell. Biol. 24 (2004) 3150-6): 5'GGGGCTACAGCACTACCTG3' and 5'GGATGGCCAGGATGATAG3'. Primers specific for alpha-1 type II collagen and aggrecan were generously provided by Dr. Carl Flannery. Annealing temperatures were 55° C. for alpha-1 type II collagen, 61.3° C. for aggrecan, 50° C. for actin, 64° C. for SVCT1, and 55° C. for SVCT2. Standard PCR procedures were used with AmpliTaq Gold DNA polymerase (Roche).

Functional Analysis of SVCT2

RNA Interference (RNAi). The RNAi transfection procedure was performed using Amaxa's Nucleofector device (Gaithersburg, Md.), the primary human chondrocyte kit (Amaxa) with the corresponding manufacturer's protocol and a total of 3 μg short interfering RNAs (siRNAs). The cell/siRNA mixture was transfected using program U24. The samples in these experiments were transfected with the following siRNAs: 1) 3 μg Silencer Negative Control #1 siRNA (Ambion, Austin, Tex.), to control for nonspecific effects, or 2) a pool of three different human SVCT2 specific siRNAs, 1 μg each of siRNA ID # 15859, # 15950, and # 15765 (Ambion). All of the SVCT2 specific siRNAs targeted both the short and full length isoforms of the SVCT2 mRNA.

The cells were incubated at 37° C./5% $CO_2$ for 68 hours after the transfection to allow the suppression of the SVCT2 mRNA expression and the turnover of pre-existing SVCT2 proteins. At this time, the samples were utilized in the AA transport assay (described above) and in parallel, samples were treated with Trizol to isolate the RNA (described above).

Real Time RT-PCR. The cDNA generated from the RNAi experiments was subjected to real time RT-PCR in order to quantify the changes in gene expression that occurred upon suppression of the SVCT2 transcript levels. The ABI Prism 7000 Sequence Detection System instrument and relative quantification software (Applied Biosystems, Foster City, Calif.) were utilized for the real time analyses. The SVCT2 primer/probe set was designed, using the ABI Prism software and the sequences available in GenBank. The following primers and probe were custom synthesized by Applied Biosystems: primer SVCT2-229F (5'GGCTTCTATGCTCGCACAGAT3'), primer SVCT2-303R (5'AAATGGGTATGGAACCTTAAACCA3'), and SVCT2-253T probe (6FAM-AGGCAAGGCGTGCTTCTGG-TAGCC-TAMRA). The real time reactions were each performed in quadruplicate in a final volume of 25 μl. The 18S rRNA reactions were set up according to the manufacturer's instructions and the SVCT2 mRNA reactions each contained 900 nM of each primer and 250 nM probe. Expression levels of SVCT2 were compared between chondrocytes from the same specimen, transfected with either the negative control siRNA or the SVCT2 siRNAs. The cDNA samples were normalized for comparison by determining 18S rRNA levels by real time RT-PCR, using the 18S-PDAR primer and probe set (Applied Biosystems). Relative quantification was calculated using the $2^{-\Delta\Delta Ct}$ formula, in which $\Delta C_T$ equals the difference between $C_T$ (cycle threshold) values for negative control and SVCT2 transfected cells (K. J. Livak and T. D. Schmittgen, Analysis of relative gene expression data using real-time quantitative PCR and the 2(−Delta Delta C(T)) Method, Methods 25 (2001) 402-8). The data is expressed as a percentage of the mean fold change in mRNA levels for the experimental samples (SVCT2 siRNAs) as compared to the calibrator (negative control siRNA).

Protein Assay. The concentration of proteins in the cell lysates from the RNAi experiments was determined using the Detergent Compatible (DC) Protein Assay (Bio-Rad, Hercules, Calif.) and a microplate reader at 750 nm.

Statistical Analyses. Statistical computations were performed using GraphPad Prism version 3.00 (GraphPad, San Diego, Calif.) and the data analysis feature of Microsoft Excel. Descriptive statistics, sample means, and standard error for all values were calculated for subgroups of interest. For descriptive purposes, pairwise comparisons between subgroups of interest were performed using analysis of variance (ANOVA) and the Newman Keuhls post hoc test or the paired t-test. A p value of <0.05 was considered significant. Kinetic analyses were performed using the GraphPad Prism software and the enzyme kinetic template.

Results

Chondrocyte expression of SVCT2. The primary human chondrocytes expressed transcripts for SVCT2 but not SVCT1 (FIG. 1, top panels). FIG. 1A (top panel) demonstrates expression of SVCT1 (360 bp fragment) in human liver but not in primary human chondrocytes. The full length SVCT2 isoform (646 bp fragment) and the short isoform (301 bp fragment), which contains a 345 bp deletion in the transcript that arises due to alternative splicing, were both expressed by primary human chondrocytes (FIG. 1B, top panel). However, the predominant isoform expressed by the chondrocytes was the full length SVCT2. Actin was successfully amplified from each sample confirming the use of equivalent amounts of intact cDNA for these comparisons (FIGS. 1A and 1B, bottom panel). The chondrocytic phenotype of these cells was confirmed by RT-PCR for the major protein components in cartilage, type II collagen and aggrecan. Both were expressed through the seventh passage, in all of the chondrocytes used in these experiments (data not shown).

Concentration of AA by chondrocytes in the context of cartilage explants. Chondrocytes, in the context of human articular cartilage explants, are able to transport and concentrate L-$^{14}$C-Asc intracellularly. The uptake of L-$^{14}$C-Asc over 21 hours by cartilage explants was determined for whole explants that were either live or dead. There was 2-fold more L-$^{14}$C-Asc found in the live explants than the dead explants (p=0.05), demonstrating active transport of AA by explants with live cells. Whole live explants contained 16.56+/−4.22 pmol L-$^{14}$C-Asc/mg tissue and dead explants contained 7.77+/−3.03 pmol L-$^{14}$C-Asc/mg tissue. After being cultured in the presence of L-$^{14}$C-Asc for 21 hours, chondrocytes were isolated from the cartilage matrix, to further distinguish AA concentrated in chondrocytes from AA trapped in the extracellular matrix. The calculated average intracellular concentration of total AA (the radiolabeled reduced form and its metabolites) was 48+/−5 mM (67 mM in superficial zone cells, 51 mM in middle zone cells, and 45 mM in deep zone cells). When compared with the media concentration of 50 μM L-$^{14}$C-Asc, on average chondrocytes concentrated total AA, in the reduced form and its metabolites, 960-fold.

Figure 2:
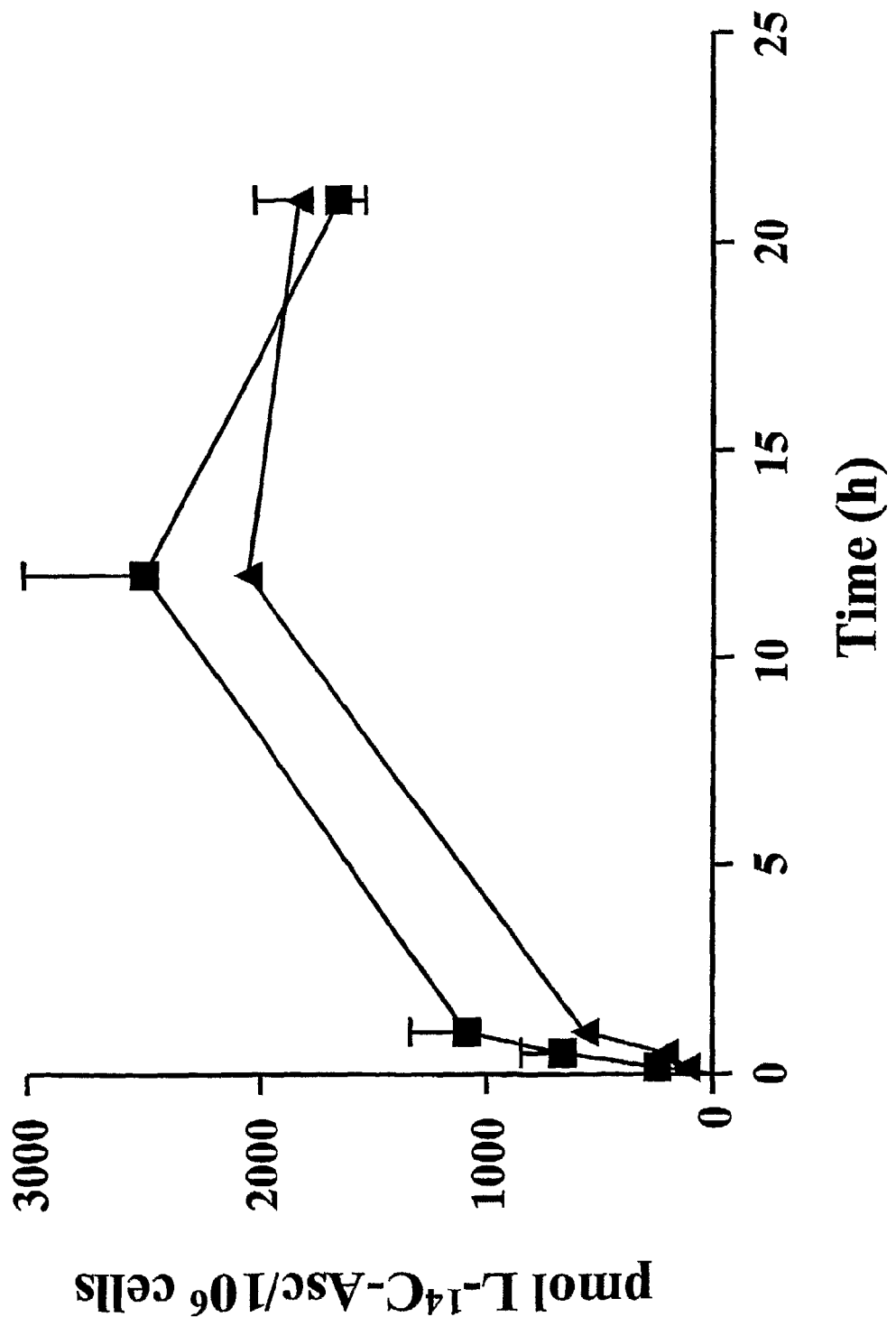
FIG. 2. Time-dependence of AA transport in passaged primary human chondrocytes. $L\text{-}^{14}C\text{-Asc}$ uptake was measured over time in the presence of sodium ($Na^+$) and presence of absence of D-glucose (Glc). The data points are expressed as the mean pmol $L\text{-}^{14}C\text{-Asc}/10^6$ cells +/− standard error (n=2-8 for each treatment). The transport buffer contained the following: ■=134 mM $Na^+$ and 10 mM glucose; ▲=134 mM $Na^+$ and no glucose.

Time-dependence of AA transport in primary human chondrocytes. The transport of L-$^{14}$C-Asc in primary human chondrocytes is dependent on both time and the presence of extracellular sodium (FIG. 2). In the presence of sodium, L-$^{14}$C-Asc transport increased significantly over a 12 hour time course. However, the measured L-$^{14}$C-Asc content inside the cells decreased slightly by 21 hours. This corresponded with the HPLC measurements of the AA concentration in the transport buffer, which indicated that only 16% of the initial AA concentration remained in the transport buffer at the 12 hour time point (data not shown). At all time points, the transport of L-$^{14}$C-Asc was independent of glucose.

Figure 3:
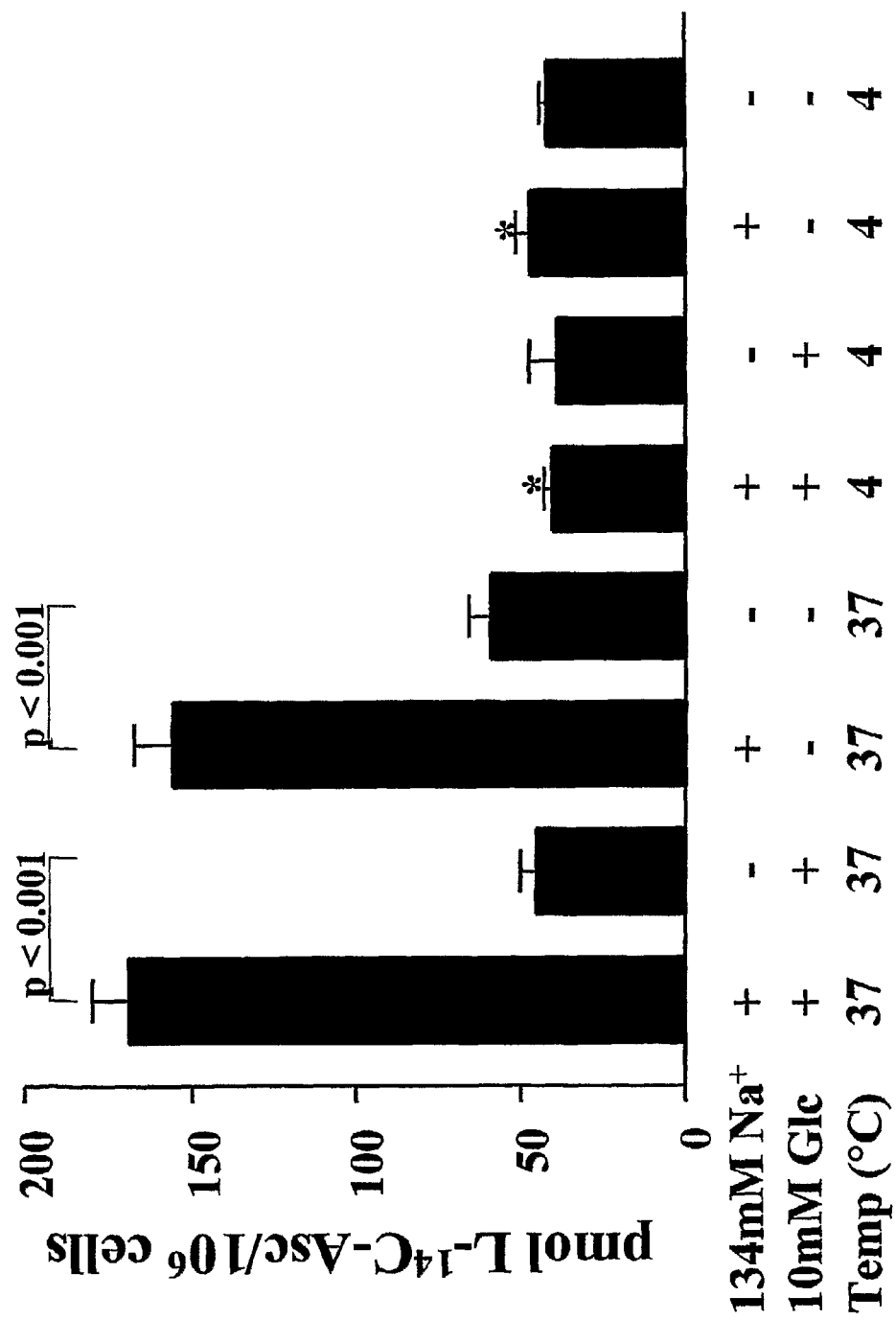
FIG. 3. Sodium-dependence and temperature-dependence of AA transport in passaged primary human chondrocytes. $L\text{-}^{14}C\text{-Asc}$ uptake was measured after 10 minutes at either 37° C. or 4° C. in the presence and absence of 134 mM sodium ($Na^+$) and/or 10 mM D-glucose (Glc). The bars indicate the mean pmol $L\text{-}^{14}C\text{-Asc}/10^6$ cells +/− standard error (n=3-16 for each treatment). *p<0.001 compared to the same treatment at 37° C.

Sodium-dependence and temperature-dependence of AA transport. To assess the sodium dependence of AA transport and to identify the active component of AA transport, the amount of L-$^{14}$C-Asc transported into primary human chondrocytes was assessed at either 37° C. or 4° C. There was approximately 3-fold more L-$^{14}$C-Asc transported in the presence of sodium than in the absence of sodium (FIG. 3; p<0.001). Additionally, in the presence of sodium, there was 3.8-fold more L-$^{14}$C-Asc transported at 37° C. than at 4° C. (p<0.001). Interestingly, the amount of L-$^{14}$C-Asc uptake at 4° C. was nearly equivalent to the amount transported in the absence of sodium at 37° C., suggesting that under these conditions, about 45 μmol L-$^{14}$C-Asc/$10^6$ cells diffuses passively into human chondrocytes in 10 minutes. HPLC measurements were also performed to verify that the cell lysates contained AA and not simply the $^{14}$C radiolabel alone. The AA concentration in the lysates measured by HPLC reflected that which was measured by radioactivity (data not shown).

Figure 4:
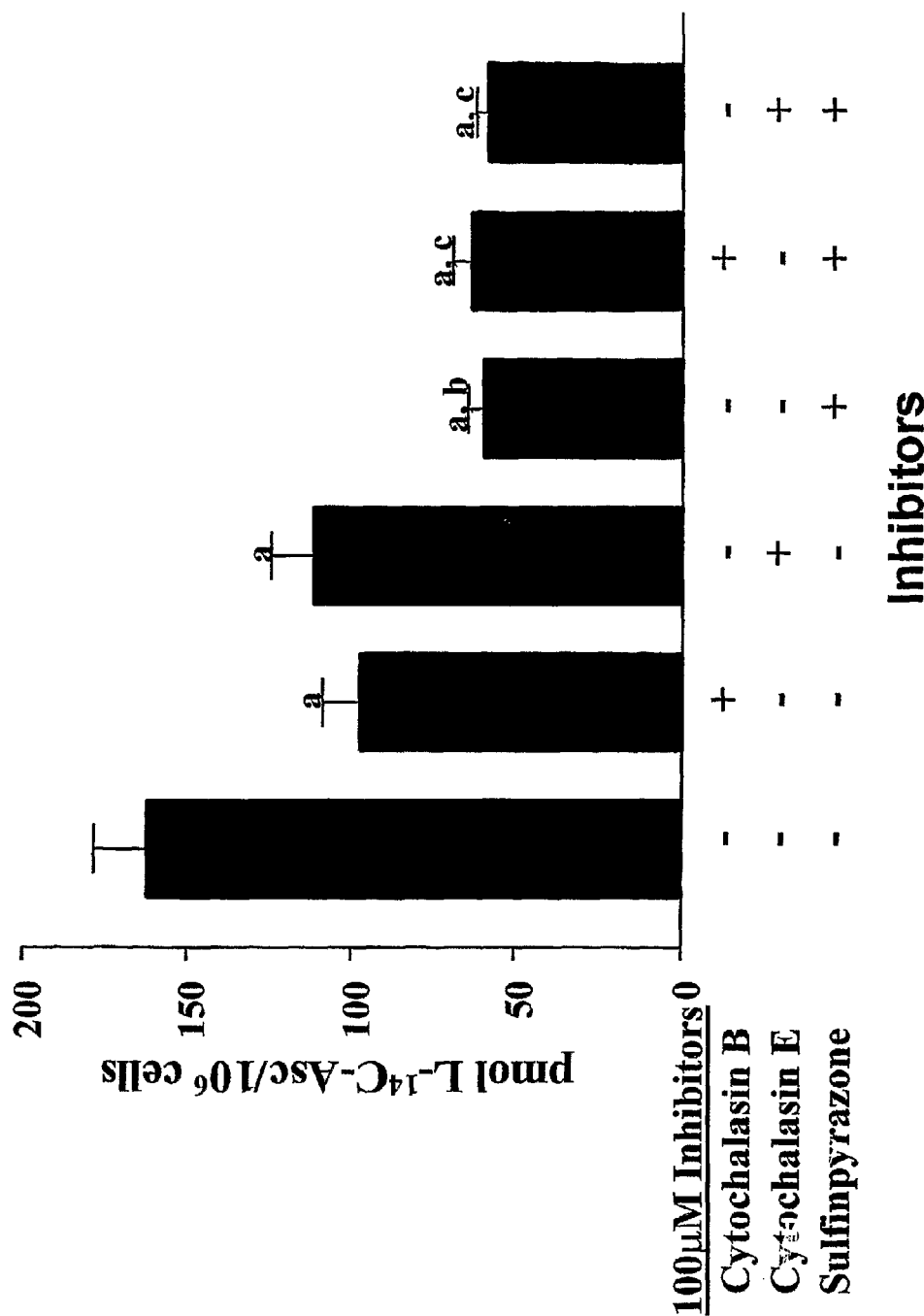
FIG. 4. Sulfinpyrazone inhibition of AA transport in passaged primary human chondrocytes. $L\text{-}^{14}C\text{-Asc}$ uptake was measured after 10 minutes in the presence of 100 µM cytochalasin B, cytochalasin E, and/or sulfinpyrazone. The bars indicate the mean pmol $L\text{-}^{14}C\text{-Asc}/10^6$ cells +/− standard error (n=8-12 for each treatment). $^a$ p<0.001 compared to the sample without inhibitor; $^b$ p<0.05 compared to the samples with Cytochalasin B or Cytochalasin E; $^c$ p<0.05 compared to the corresponding samples with Cytochalasin B or Cytochalasin E alone.

Sulfinpyrazone inhibition of AA transport. The transport of L-$^{14}$C-Asc into primary human chondrocytes was inhibited approximately 65% by the anion transport inhibitor sulfinpyrazone (p<0.001; FIG. 4). Cytochalasin B, a specific inhibitor of the GLUTs and of actin polymerization, decreased the transport of L-$^{14}$C-Asc by 40% (p<0.001). However, cytochalasin E, a control for the actin effects of cytochalasin B, suppressed L-$^{14}$C-Asc transport to a similar degree (35%, p<0.001). The treatment of chondrocytes with either cytochalasin B or cytochalasin E in combination with sulfinpyrazone did not suppress the level of L-$^{14}$C-Asc uptake beyond the level achieved with sulfinpyrazone alone. Thus, the effects of the cytochalasins can be attributed to an alteration in chondrocyte actin polymerization rather than an inhibition of transport via the GLUTs. In contrast, sulfinpyrazone significantly decreased the uptake of L-$^{14}$C-Asc when compared to either of the cytochalasins (p<0.05). In fact, the sulfinpyrazone treatment decreased the uptake of L-$^{14}$C-Asc to the level of L-$^{14}$C-Asc uptake observed at 4° C. and in the absence of sodium (FIG. 3), representing passive uptake alone. These results taken together suggest that transport of AA by human chondrocytes is mediated by an anion transporter.

Figure 5:
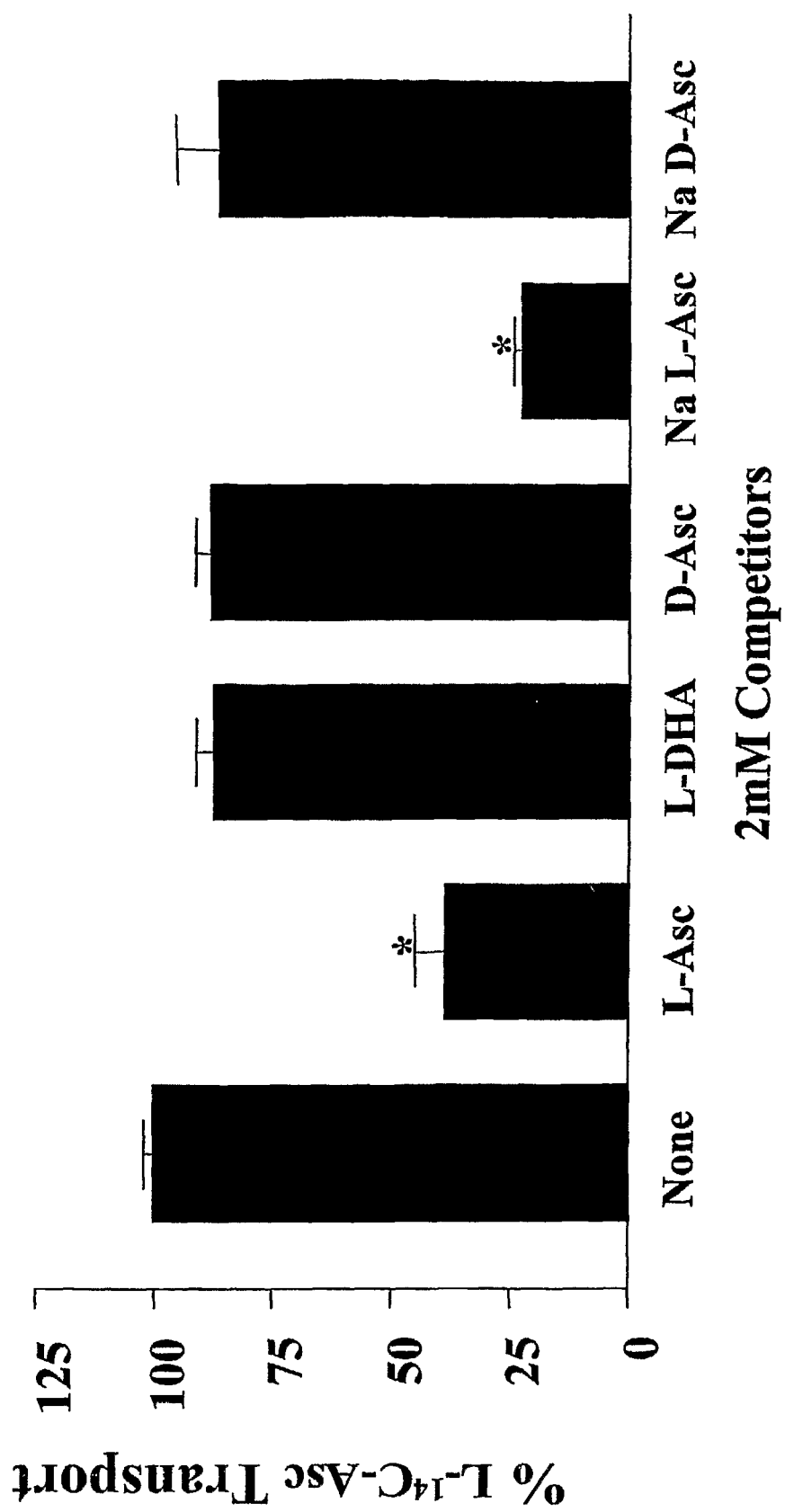
FIG. 5. Stereoselective transport of the L-forms of AA in passaged primary human chondrocytes. $L\text{-}^{14}C\text{-Asc}$ uptake was measured after 10 minutes in the presence of 2 mM of the following unlabeled competitors: no competitor; L-ascorbic acid (L-Asc); dehydroascorbic acid (L-DHA); D-isoascorbic acid (D-Asc); Na L-ascorbate (Na L-Asc); or Na D-isoascorbate (Na D-Asc). The bars indicate the mean percentage of L-$^{14}$C-Asc transported +/− standard error (n=9-11 for each treatment). The amount of L-$^{14}$C-Asc transported in the samples without competitor was set to 100%. *p<0.001 compared to the sample with no competitor.

Stereoselective transport of the L-forms of AA. To determine the stereospecificity of AA uptake by chondrocytes, the L-$^{14}$C-Asc uptake assay was performed in the presence of various AA forms (FIG. 5). Only the L-forms of AA were able to effectively compete with L-$^{14}$C-Asc transport. L-Asc was able to suppress L-$^{14}$C-Asc transport by approximately 60%, as compared to the sample with no competitor (p<0.001). Furthermore, Na L-Asc was able to decrease the transport of L-$^{14}$C-Asc by 75% (p<0.001). On the other hand, the oxidized form of AA, DHA, and the D-forms of AA, D-Asc and Na D-Asc, were unable to effectively compete with L-$^{14}$C-Asc for transport into the cells. These results demonstrate stereospecificity of AA transport by chondrocytes.

Figure 6B:
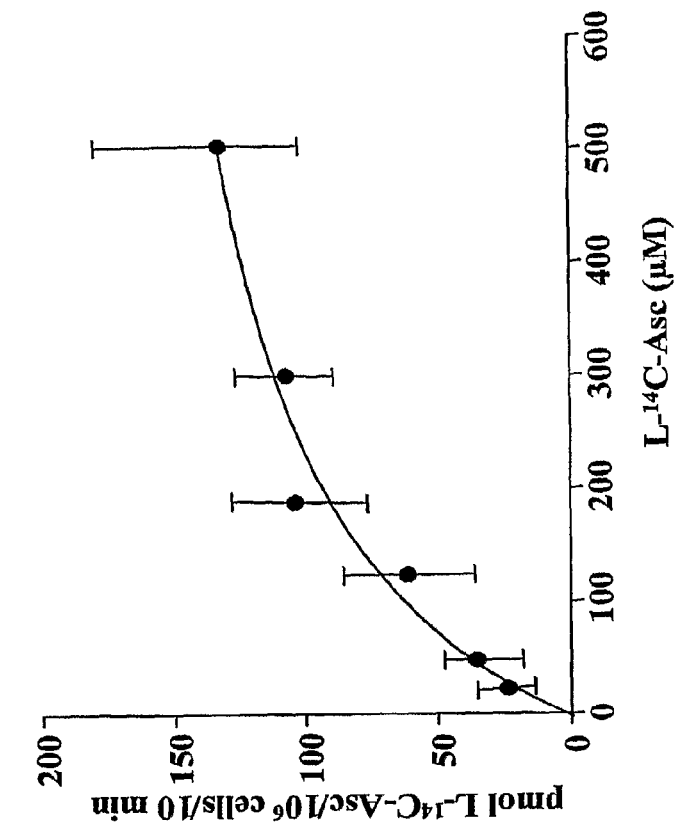
FIG. 6. AA transport kinetics in passaged primary human chondrocytes. (A) Saturability of active AA transport. The intracellular uptake of 200 μM L-$^{14}$C-Asc was measured after 10 minutes in the presence of increasing concentrations of unlabeled L-ascorbic acid (L-Asc). The data points indicate the mean pmol L-$^{14}$C-Asc/10$^6$ cells +/− standard error (n=3 for each treatment). (B) Michaelis-Menten kinetics of AA transport. The intracellular uptake of 0-500 μM L-$^{14}$C-Asc was measured after 10 minutes in the presence of 100 μM unlabeled L-ascorbic acid. The data points indicate the mean velocity (pmol L-$^{14}$C-Asc/10$^6$ cells/10 minutes) at the given concentration of L-$^{14}$C-Asc. This is a representative experiment where each condition was performed in triplicate and the bars indicate the range of velocities for each concentration.
Figure 6A:
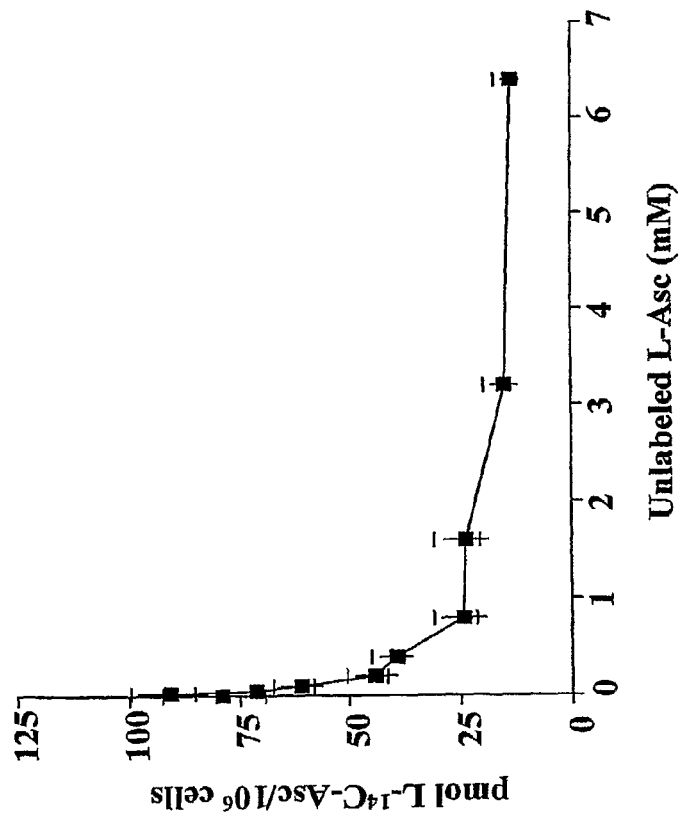

AA transport kinetics. The transport of L-$^{14}$C-Asc was measured in the presence of increasing concentrations of unlabeled L-Asc in order to assess the saturability of the transport mechanism (FIG. 6A). The addition of unlabeled L-Asc strongly competed for the transport of L-$^{14}$C-Asc until approximately 1000 μM L-Asc had been added. At concentrations above 1000 μM, the transporter was fully saturated and there was no further decrease in the amount of L-$^{14}$C-Asc that was transported into the cells. In order to determine the kinetic properties of the active AA uptake mechanism, chondrocytes were incubated with increasing concentrations of L-$^{14}$C-Asc at 37° C. and 4° C. FIG. 6B is a representative Michaelis-Menten plot that shows an increase in AA uptake with increasing concentrations of L-$^{14}$C-Asc. The vMax for AA transport in chondrocytes was 148+/−35 pmol L-$^{14}$C-Asc/$10^6$ cells/10 minutes and the $K_m$ was 179+/−17 µM.

Figures 7A, 7B:
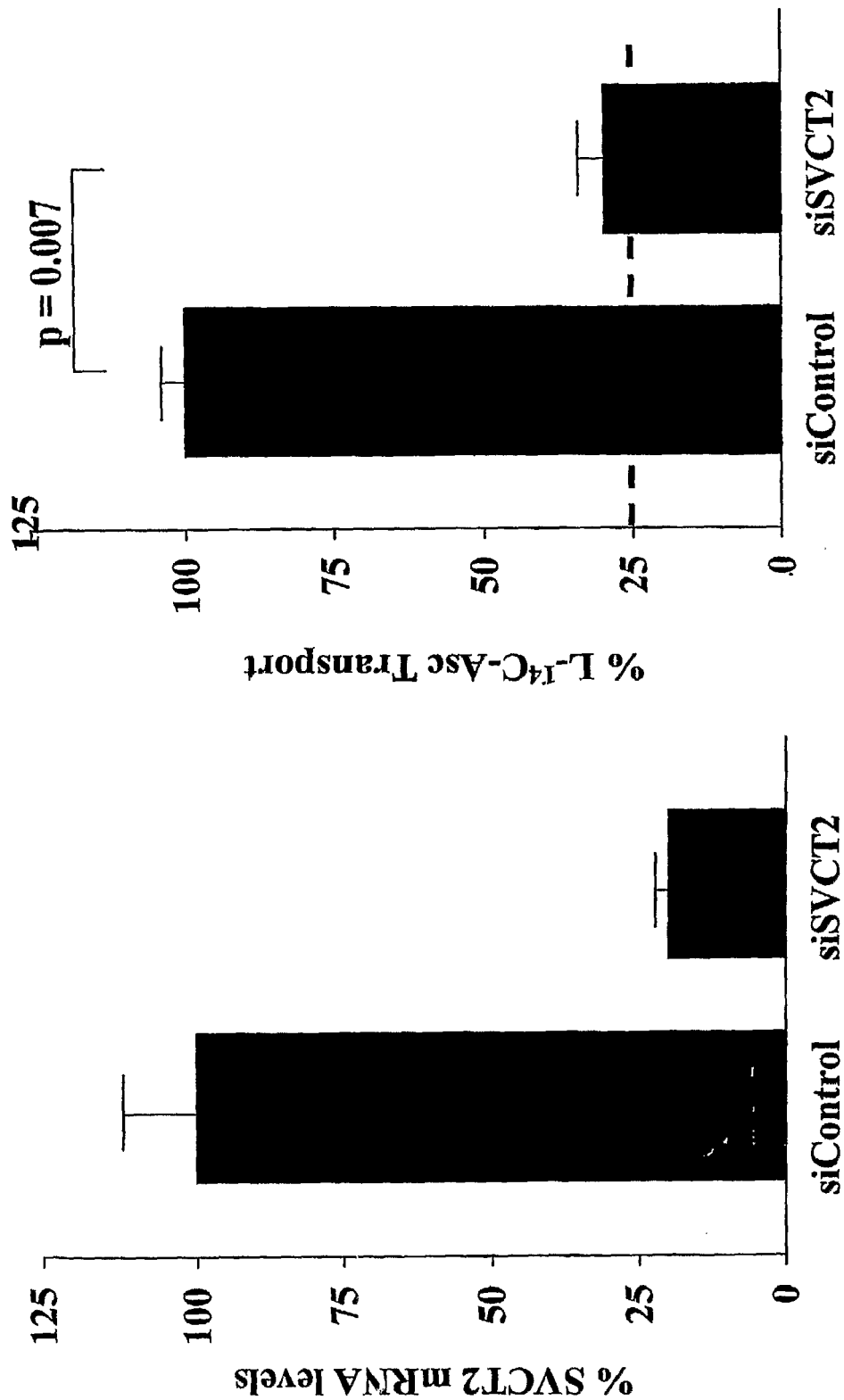
FIG. 7. Suppression of SVCT2 expression by RNAi. Passaged primary human chondrocytes were transfected with a negative control siRNA (siControl) or siRNAs specific for SVCT2 (siSVCT2). SVCT2 steady-state mRNA levels and AA uptake were assessed in these cells 68 hours post transfection. (A) SVCT2 mRNA levels by real-time RT-PCR in siRNA transfected cells. The bars indicate the mean SVCT2 mRNA level +/− the 95% confidence level (n=4 for each treatment), expressed as a percentage of the negative control (the mRNA level in cells transfected with the negative control siRNA and designated as 100%). (B) AA transport in siRNA transfected cells. The bars indicate the mean L-$^{14}$C-Asc transport level (+/− standard error) expressed as a percentage of the negative control (the amount of L-$^{14}$C-Asc transported in cells transfected with the negative control siRNA and designated as 100%). The level of transport that is assumed to occur by passive diffusion in primary chondrocytes is indicated by a dashed line. This is a representative experiment where each condition was performed in duplicate.

Suppression of SVCT2 expression by RNAi. To assess the role of the SVCT2 transporter in mediating AA transport in primary human chondrocytes, we suppressed the expression of SVCT2, with sequence specific siRNAs (FIG. 7). The SVCT2 mRNA levels were decreased approximately 80% by the SVCT2 siRNAs, as compared to the negative control (FIG. 7A). As shown in FIG. 7B, this decrease in mRNA levels resulted in a 75% decrease in the transport of L-$^{14}$C-Asc in the SVCT2 siRNA treated samples (p=0.007). Thus, suppression of SVCT2 alone fully inhibited the active component of L-$^{14}$C-Asc transport and reduced L-$^{14}$C-Asc uptake to levels attributable to passive diffusion (as shown in FIG. 3 and indicated by the dashed line in FIG. 7B). These results demonstrate that SVCT2 mediates and fully accounts for the active component of AA transport in primary human chondrocytes.

EXAMPLE 3

Dehydroascorbate Transport in Human Chondrocytes is Regulated by Hpoxia and is a Physiologically Relevant Source of Ascorbic Acid in the Joint Materials and Methods:

Chondrocyte Isolation and Cell Culture. Articular cartilage was obtained from human knee surgical waste tissues at the time of knee replacement surgery (n=7). Primary human chondrocytes were isolated from cartilage specimens, which were harvested from non-lesioned areas. For each specimen, the cartilage was minced and the chondrocytes isolated by enzymatic digestion, similar to methods published previously (Kuettner K. et al. Synthesis of cartilage matrix by mammalian chondrocytes in vitro. I. Isolation, culture characteristics, and morphology. J. Cell Biol. 1982; 93(3):743-750). Cells at each passage were tested, using reverse transcription polymerase chain reaction (RT-PCR), for the expression of the chondrocytic genes, type II collagen and aggrecan.

Dehydroascorbate Transport Assay in Isolated Primary Human Chondrocytes. DHA transport was measured using a modified version of the uptake assay published by Wilson and Dixon (Wilson J X, Dixon S J. High-Affinity Sodium-Dependent Uptake of Ascorbic Acid by Rat Osteoblasts. J. Mem. Biol. 1989; 111:83-91). Primary human chondrocytes were seeded at a density of 4.5×$10^5$ cells/well on a 6-well plate. Prior to the transport assay, cells were plated for 48 hours in DMEM/F12, containing 10% FCS but no AA or DHA. Cells were washed in transport buffer containing: 134 mM LiCl, 5.4 mM KCl, 1.8 mM $CaCl_2$, 0.8 mM $MgSO_4$, 20 mM HEPES, pH 7.3 with KOH. DHA uptake was assessed by incubating the chondrocytes in transport buffer containing 189 µM L-$^{14}$C-dehydroascorbate (L-$^{14}$C-DHA). Stock solutions of L-$^{14}$C-DHA were generated immediately before use by incubating L-$^{14}$C-ascorbic acid (L-$^{14}$C-AA; 4 mCi/mmol; NEN, Boston, Mass.) in 0.4 mM homocysteine with an AA oxidase spatula (Roche Diagnostics, Mannheim, Germany) for 15 minutes, stirring at room temperature. The standard DHA transport assay conditions were 37° C./5% $CO_2$/21% $O_2$ for 10 min. DHA uptake was terminated by washing the cells four-times in ice-cold PBS. The cells were lysed with Puregene Cell Lysis Solution (Gentra Systems) and scintillation counting was performed in Uniscint BD (National Diagnostics). The total pmol of L-$^{14}$C-DHA transported was calculated using the total dpm of L-$^{14}$C-DHA transported and the specific activity of the radiolabel.

We performed DHA transport assays under various conditions designed to augment or inhibit the function of the DHA transporters, including variations of the following: +/−134 mM $Na^+$; +/−10 mM, 50 mM, or 100 mM D-glucose; temperature (4° C. or 37° C.); 0.1 mM Cytochalasin B (Sigma) and 0.1 mM Cytochalasin E (Sigma); 2 mM unlabeled L-dehydroascorbate (L-DHA), D-dehydroascorbate (D-DHA), Na L-dehydroascorbate (Na L-DHA), Na D-dehydroascorbate (Na D-DHA), L-ascorbic acid (L-AA, Sigma), D-isoascorbic acid (D-AA, Aldrich), Na L-ascorbate (Na L-AA, Sigma), and Na D-isoascorbate (Na D-AA, Aldrich); and 1%, 2.5%, 5%, and 21% $O_2$ for 24 or 72 hours. Cytochalasin B inhibits DHA transport via the GLUTs (Deves R, Krupka R M. Cytochalasin B and the kinetics of inhibition of biological transport: a case of asymmetric binding to the glucose carrier. Biochim. Biophys. Acta 1978; 510(2):339-48) and also inhibits actin polymerization, while cytochalasin E has no known inhibitory effects on transport mechanisms, but also inhibits actin polymerization and thus is a control for the actin effects of cytochalasin B. The properties of the AA forms used in these experiments were discussed in detail previously (Clark A G, et al. The effects of ascorbic acid on cartilage metabolism in guinea pig articular cartilage explants. Matrix Biol. 2002; 21:175-184). Stock solutions of different unlabeled DHA forms were generated in the same manner as the L-$^{14}$C-DHA.

High Performance Liquid Chromatography (HPLC). The integrity of the L-$^{14}$C-DHA stocks utilized in these experiments was determined by measuring the proportion of AA and DHA by HPLC. AA was measured with an electrochemical detector (EC), using the method of Lee et al. (Lee W, et al. Ascorbic acid in lymphocytes: cell preparation and liquid-chromatographic assay. Clin. Chem. 1982; 28(10):2165-9). The amount of DHA in the stocks and samples was determined by reducing the DHA to AA, as previously described (Behrens W A, Madere R. A highly sensitive high-performance liquid chromatography method for the estimation of ascorbic and dehydroascorbic acid in tissues, biological fluids, and foods. Anal. Biochem. 1987; 165(1):102-7).

RNA Isolation. Monolayer cells were grown to confluency on 35 mm plates and the cells were lysed, using 1 ml of Trizol reagent (Gibco). The RNA extraction procedure was carried out, according to the manufacturer's protocol through the phase separation step. The aqueous phase was transferred to a new tube and 10 µg tRNA (Sigma) was added. Then 0.5 ml isopropanol was added and the sample was frozen overnight at −80° C. The RNA was pelleted at 13,000 rpm for 20 min at 4° C., the liquid phase was discarded, and the pellet was air dried. The RNA was then processed, according to the manufacturer's protocol for the Qiagen RNeasy kit (Qiagen, Valencia, Calif.).

RT-PCR. Total RNA was reverse transcribed into complementary DNA (cDNA), using Superscript II Reverse Transcriptase (Gibco) and random hexamer primers. The use of random hexamers allowed the amplification of 18S ribosomal RNA as a control. Intron spanning primers were designed for GLUT1 (Shikhman A R, et al. Cytokine regulation of facilitated glucose transport in human articular chondrocytes. J. Immunol. 2001; 167(12):7001-8), GLUT3 (Shikhman A R, et al. Cytokine regulation of facilitated glucose transport in human articular chondrocytes. J. Immunol. 2001; 167(12): 7001-8), GLUT6 (5'TTGCTGCCAACCTGACTCTG3' and 5'GTCCTTCACGCAAGGGAAAG3'), GLUT8 (5'ACATCTCCGAAATCGCCTAC3' and 5'CCGATGATGAAGGGCTTGTA3'), GLUT9 (5' TGCTGAGCCTTC- CCTTTCTC3' and 5'CCACTGCAGAAAGAGGCGAT3'), GLUT10 (5'AGGACCAATGAGGACCAAAG3' and 5'AGGAAGGAGAGGCTGATGAA3'), and GLUT11 (5'TCATCAATGCCCCGACCTTG3' and 5'TCATTCCCG-CAGAGCTCCAT3') corresponding to the human sequences available in Genbank. Primers specific for alpha-1 type II collagen and aggrecan were generously provided by Dr. Carl Flannery. Annealing temperatures were 50° C. for GLUT1, 58° C. for GLUT3, 68° C. for GLUT6 and GLUT9, 65° C. for GLUT8 and GLUT10, 71° C. for GLUT11, 55° C. for alpha-1 type II collagen, and 61.3° C. for aggrecan. Standard PCR procedures were used with AmpliTaq Gold DNA polymerase (Roche).

Functional Analysis of GLUT1 and GLUT3. RNA Interference (RNAi)—The RNAi transfection procedure was performed using Amaxa's Nucleofector device (Gaithersburg, Md.), the primary human chondrocyte kit (Amaxa), and a total of 3 µg short interfering RNAs (siRNAs). Chondrocytes were transfected on program U24 with the following siRNAs: 1) 3 µg Silencer Negative Control #1 siRNA (Ambion, Austin, Tex.), to control for nonspecific effects, 2) a pool of three different human GLUT1 specific siRNAs, 1 µg each of siRNA ID # 17981, # 18074, and # 18160 (Ambion), or 3) a pool of two different human GLUT3 specific siRNAs, 2.5 µg each of siRNA ID # 18786 and # 18882 (Ambion). The cells were incubated at 37° C./5% $CO_2$/21% $O_2$ for 65-72 hrs after the transfection to allow the suppression of the GLUT1 and GLUT3 mRNA expression and turnover of pre-existing GLUT proteins. The cells were subsequently analyzed for DHA transport (described above) or treated with Trizol to isolate the RNA for real time RT-PCR.

Real Time RT-PCR—The cDNA generated from the RNAi experiments was subjected to real time RT-PCR in order to quantify the changes in gene expression that occurred upon suppression of the GLUT1 and GLUT3 transcript levels. The ABI Prism 7000 Sequence Detection System instrument and relative quantification software (Applied Biosystems, Foster City, Calif.) were utilized for the real time analyses. The real time reactions were each performed in quadruplicate in a final volume of 25 µl, according to the manufacturer's instructions. Expression levels of GLUT1 and GLUT3 were compared between chondrocytes from the same specimen, transfected with either the negative control siRNA or the GLUT1 or GLUT3 siRNAs. Transcript levels were determined by real time RT-PCR, using the following Applied Biosystems primer and probe sets: 18S-PDAR (18S rRNA), Hs00197884_m1 (GLUT1), and Hs00359840_m1 (GLUT3). GLUT1 and GLUT3 mRNA levels were normalized to 18S rRNA levels and relative quantification was determined by the $2^{-\Delta\Delta Ct}$ formula, in which $\Delta C_T$ equals the difference between $C_T$ (cycle threshold) values for negative control and GLUT1 or GLUT3 transfected cells (Livak K J, Schmittgen T D. Analysis of relative gene expression data using real-time quantitative PCR and the 2(-Delta Delta C(T)) Method. Methods 2001; 25(4):402-8) The data is expressed as a percentage of the mean fold change in mRNA levels for the experimental samples (GLUT1 or GLUT3 siRNAs) as compared to the calibrator (negative control siRNA).

Protein Assay—The concentration of proteins in the cell lysates from the RNAi experiments was determined using the Detergent Compatible (DC) Protein Assay (Bio-Rad, Hercules, Calif.).

Synovial Fluid and Plasma Collection. Synovial fluid and plasma were drawn from a subset of 23 participants in the POP study (Prediction of Osteoarthritis Progression) with the approval of the Duke Institutional Review Board. All participants had symptomatic knee osteoarthritis (OA) with radiographic severity by Kellgren Lawrence (KL) grading (Kellgren J H, Lawrence J S. Radiological assessment of osteo-arthrosis. Ann Rheum Dis 1957; 16(4):494-502) of 1 to 4. Joint fluid was aspirated from both knees, when feasible, and plasma was drawn concurrently. Samples were collected into either cold perchloric acid (to stabilize AA) (Behrens W A, Madere R. A highly sensitive high-performance liquid chromatography method for the estimation of ascorbic and dehydroascorbic acid in tissues, biological fluids, and foods. Anal. Biochem. 1987; 165(1):102-7) or were drawn into empty tubes on ice. Within 90 minutes, homocysteine was added to the untreated samples and incubated at room temperature for 30 minutes to reduce DHA to AA for a total Asc measurement (31), followed by the addition of cold perchloric acid. All samples were frozen at −80° C. until HPLC (see procedure above) was performed in order to determine the amount of AA and DHA in the samples. The synovial fluid samples from a total of 33 knees were included in this study.

Statistical Analyses. Statistical computations were performed using GraphPad Prism version 3.00 (GraphPad, San Diego, Calif.) and the data analysis feature of Microsoft Excel. Descriptive statistics, sample means, and standard error for all values were calculated for subgroups of interest. For descriptive purposes, pairwise comparisons between subgroups of interest were performed using analysis of variance (ANOVA) and the Newman Keuhls post hoc test or the paired t-test. A p value of <0.05 was considered significant. The percentages of AA and DHA in synovial fluid and blood from osteoarthritic patients in this study were compared to percentages reported in the literature for non-arthritic samples and patients with rheumatoid arthritis (RA) (Lunec J, Blake D R. The determination of dehydroascorbic acid and ascorbic acid in the serum and synovial fluid of patients with rheumatoid arthritis (RA). Free Rad. Res. Comm. 1985; 1(1):31-9).

Results:

Glucose transporter expression. Primary human chondrocytes expressed transcripts for all seven of the glucose transporters analyzed: GLUT1, GLUT3, GLUT6, GLUT8, GLUT9, GLUT10, and GLUT11 (data not shown). The chondrocytic phenotype of these cells was confirmed by RT-PCR, showing mRNA expression of the major protein components in cartilage, type II collagen and aggrecan, at all of the cell passages used for these experiments (data not shown).

Figures 8A, 8B:
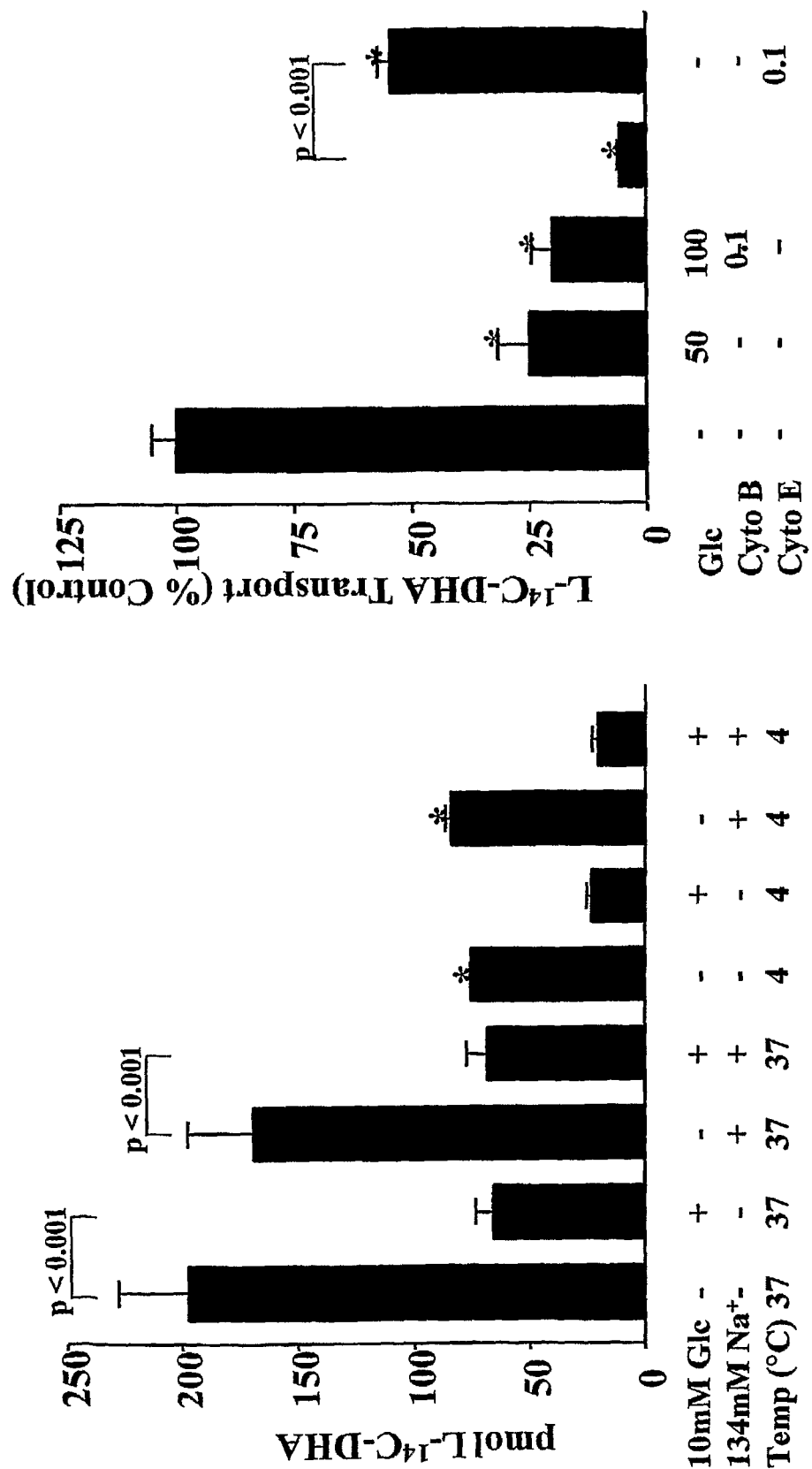
FIG. 8: Glucose-suppression, Temperature-dependence, and Cytochalasin B Inhibition of DHA Transport. A. L-$^{14}$C-DHA uptake was measured after 10 min at either 37° C. or 4° C. in the presence and absence of 134 mM sodium (Na$^+$) and/or 10 mM D-glucose (Glc). The bars indicate the mean pmol L-$^{14}$C-DHA/4.5×10$^5$ cells +/− standard error. *p<0.001 compared to the same treatment at 37° C. B. Glucose and Cytochalasin B Inhibition of DHA Transport. L-$^{14}$C-DHA uptake was measured after 10 min in the presence of 50 mM D-glucose (Glc), 100 mM D-glucose, 0.1 mM cytochalasin B (Cyto B), or 0.1M cytochalasin E (Cyto E). The bars indicate the mean percentage of L-$^{14}$C-DHA transport +/− standard error. The amount of L-$^{14}$C-DHA transported in the samples without inhibitor was set to 100%. *p<0.001 compared to the sample without inhibitor.

Glucose-suppression, temperature-dependence, and cytochalasin B inhibition of DHA transport. The transport of DHA into primary human chondrocytes was highest in the absence of glucose at 37° C. (FIG. 8A). DHA transport was suppressed 66% by 10 mM glucose at both 37° C. (p<0.001) and 4° C. and up to 80% by 100 mM glucose (FIG. 8B, p<0.001). Passive diffusion of DHA into chondrocytes, represented by transport at 4° C. in the presence of 10 mM glucose, constituted 11% of transport under optimized conditions (37° C. without glucose). There was no statistically significant reduction of DHA transport by sodium in the presence or absence of glucose, although in the absence of glucose, there was a slight inhibitory effect (FIG. 8A). Therefore, the sodium independence and the inhibition of DHA transport by glucose at both 37° C. and 4° C., suggested a passive uptake mechanism compatible with sodium independent GLUT mediated transport.

In addition to a dose-dependent inhibition of DHA transport by glucose, the transport of DHA into primary human chondrocytes was inhibited 95% by cytochalasin B (p<0.001), a specific inhibitor of the GLUTs and of actin polymerization. Cytochalsin E, a control for the actin effects of cytochalasin B, suppressed DHA transport 40% (p<0.001). Thus, the majority of the inhibition of DHA transport by cytochalasin B was attributable to inhibition of the GLUTs. The cytochalasin B treatment decreased the transport of L-$^{14}$C-DHA to the level representing passive diffusion alone. These results taken together suggested that transport of DHA by human chondrocytes was mediated entirely by GLUTs.

Figure 9:
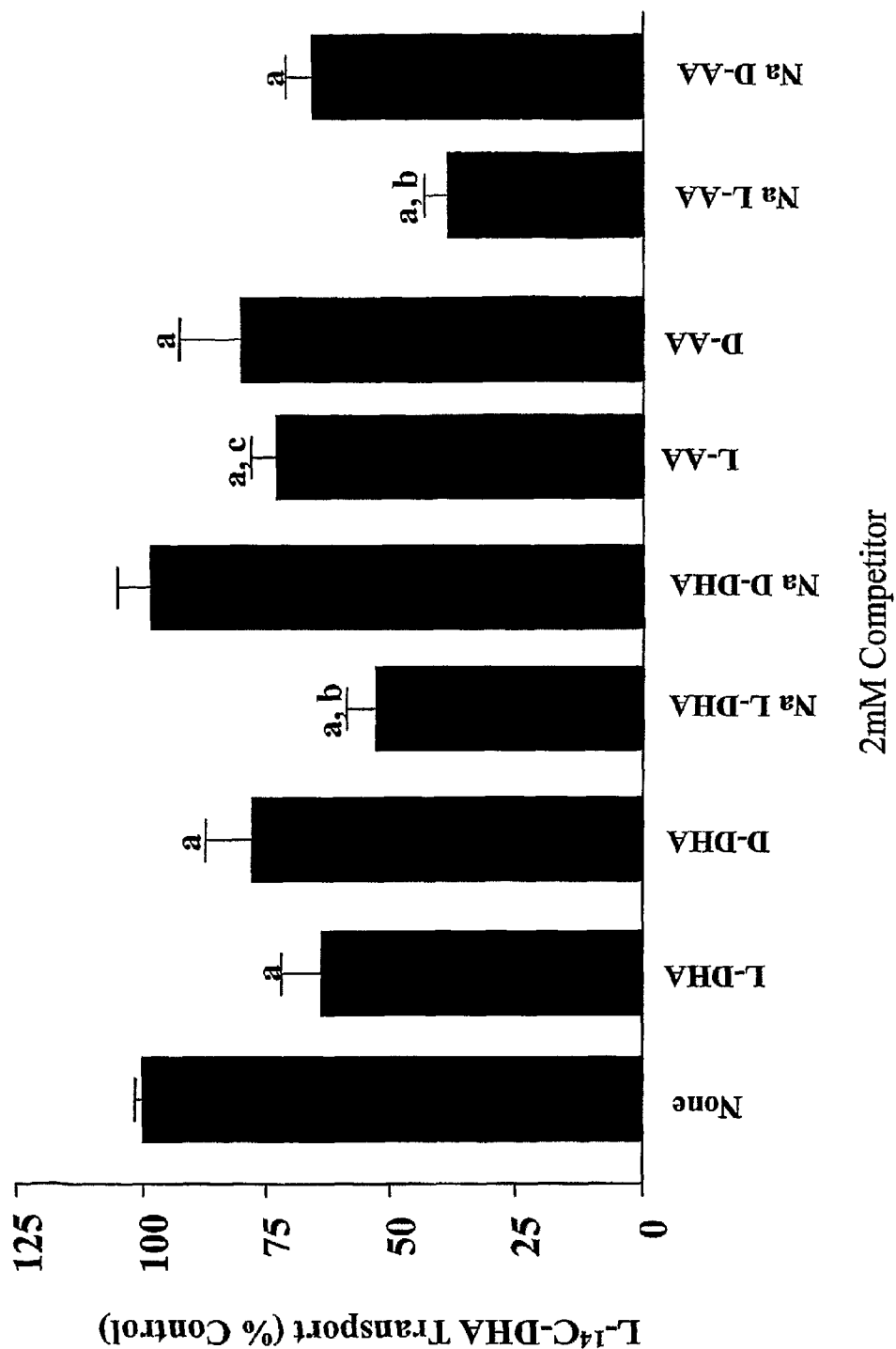
FIG. 9: Modest Stereoselective Transport of the L-forms of DHA. L-$^{14}$C-DHA uptake was measured after 10 min in the presence of 2 mM of the following unlabeled competitors: no competitor (None); L-dehydroascorbate (L-DHA); D-dehydroascorbate (D-DHA); Na L-dehydroascorbate (Na L-DHA); Na D-dehydroascorbate (Na D-DHA); L-ascorbic acid (L-AA); D-isoascorbic acid (D-AA); Na L-ascorbate (Na L-AA); or Na D-isoascorbate (Na D-AA). The bars indicate the mean percentage of L-$^{14}$C-DHA transported +/− standard error. The amount of L-$^{14}$C-DHA transported in the samples without competitor was set to 100%. a: p<0.05 compared to the sample with no competitor. b: p<0.05 compared to the sample with the corresponding D-form. c: p<0.001 compared to Na L-AA.

Modest stereoselective transport of the L-forms of DHA. To determine the stereospecificity of DHA uptake by chondrocytes, the L-$^{14}$C-DHA uptake assay was performed in the presence of various DHA and AA forms (FIG. 9). The following isoforms were able to effectively compete with L-$^{14}$C-DHA transport: L-DHA, D-DHA, Na L-DHA, L-AA, D-AA, Na L-AA, and Na D-AA (p<0.05). Only Na D-DHA was unable to compete with L-$^{14}$C-DHA for transport into chondrocytes. Additionally, Dixon plot analyses demonstrated that L-AA and D-AA were non-competitive inhibitors of L-$^{14}$C-DHA transport (data not shown). The L-forms of both DHA and AA were able to compete more efficiently for transport into primary human chondrocytes, than the D-forms of both DHA and AA. Generally, the sodium containing forms of both DHA and AA were able to compete more efficiently for transport into primary human chondrocytes, than the sodium free forms of both DHA and AA. Overall, these results demonstrated modest L-form stereospecificity of DHA transport by chondrocytes.

Figures 10A, 10B:
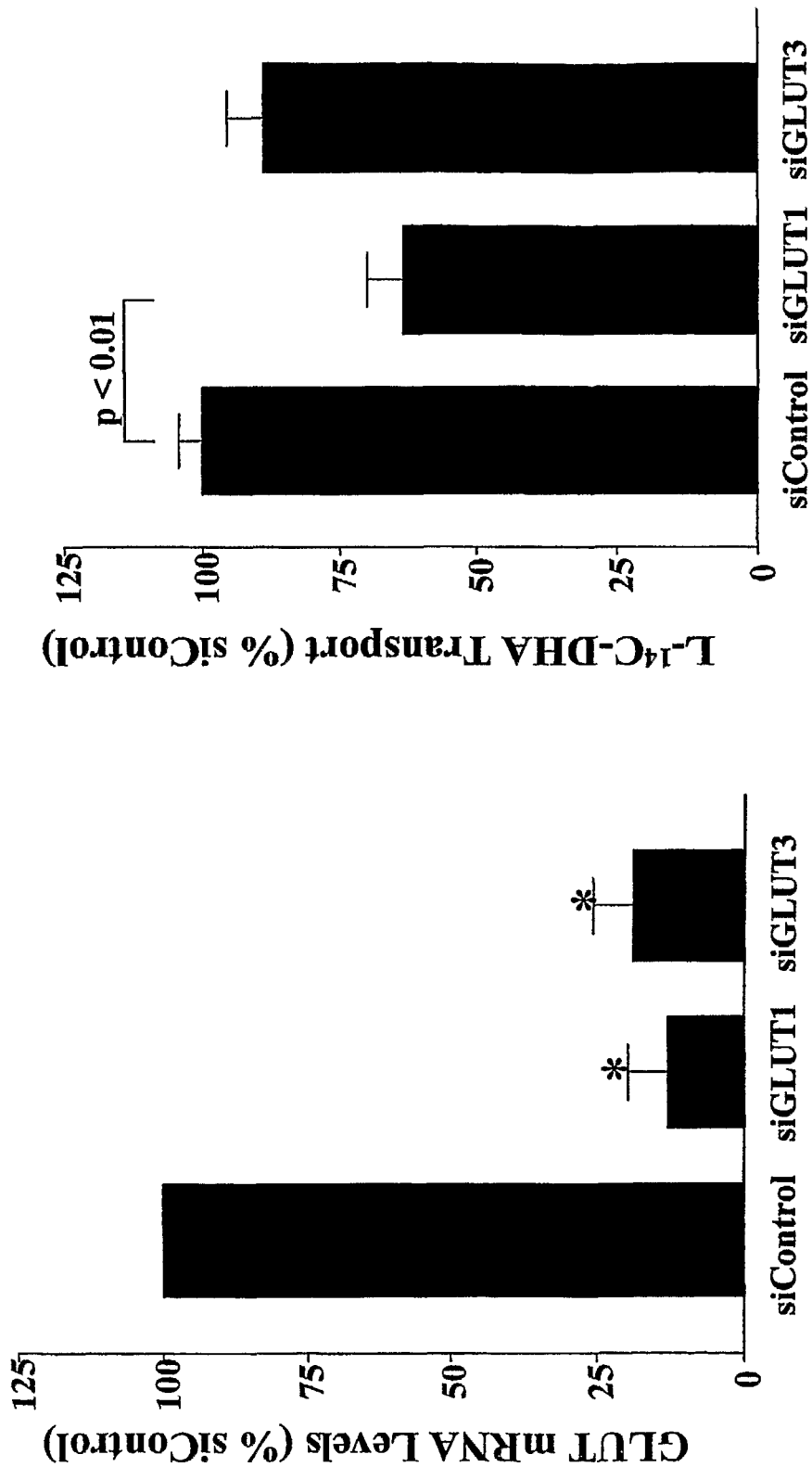
FIG. 10: Suppression of GLUT1 and GLUT3 Expression by RNAi. Primary human chondrocytes were transfected with a negative control siRNA (siControl) or siRNAs specific for GLUT1 (siGLUT1) or GLUT3 (siGLUT3). GLUT1 and GLUT3 steady-state mRNA levels and DHA uptake were assessed in these cells 65-72 hours post transfection. A. GLUT1 and GLUT3 mRNA Levels by Real Time RT-PCR in siRNA Transfected Cells. The bars indicate the mean GLUT1 or GLUT3 mRNA levels expressed as a percentage of the negative control (the mRNA level in cells transfected with the negative control siRNA and designated as 100%). *p<0.01 compared to the negative control (siControl). B. DHA Transport in siRNA Transfected Cells. The bars indicate the mean DHA transport level (+/− standard error) expressed as a percentage of the negative control (the amount of DHA transport in cells transfected with the negative control siRNA and designated as 100%).

Suppression of GLUT1 and GLUT3 expression by RNAi. To assess the role of GLUT1 and GLUT3 in mediating DHA transport in primary human chondrocytes, we suppressed the expression of GLUT1 and GLUT3 with sequence specific siRNAs (FIG. 3). The GLUT1 mRNA levels were decreased approximately 90% by the GLUT1 siRNAs, as compared to the negative control (FIG. 10A, p<0.01). The GLUT3 transcript levels were suppressed approximately 80% by the GLUT3 siRNAs (p<0.01). As shown in FIG. 10B, the decrease in GLUT1 mRNA levels resulted in a 37% decrease in the transport of DHA (p<0.01), while the suppression of GLUT3 mRNA levels resulted in a 12% decrease in DHA transport. Thus, suppression of GLUT1 accounted for a portion of the DHA transport in human chondrocytes, while GLUT3 suppression had only a minimal effect on the uptake of DHA in chondrocytes.

Figure 11B:
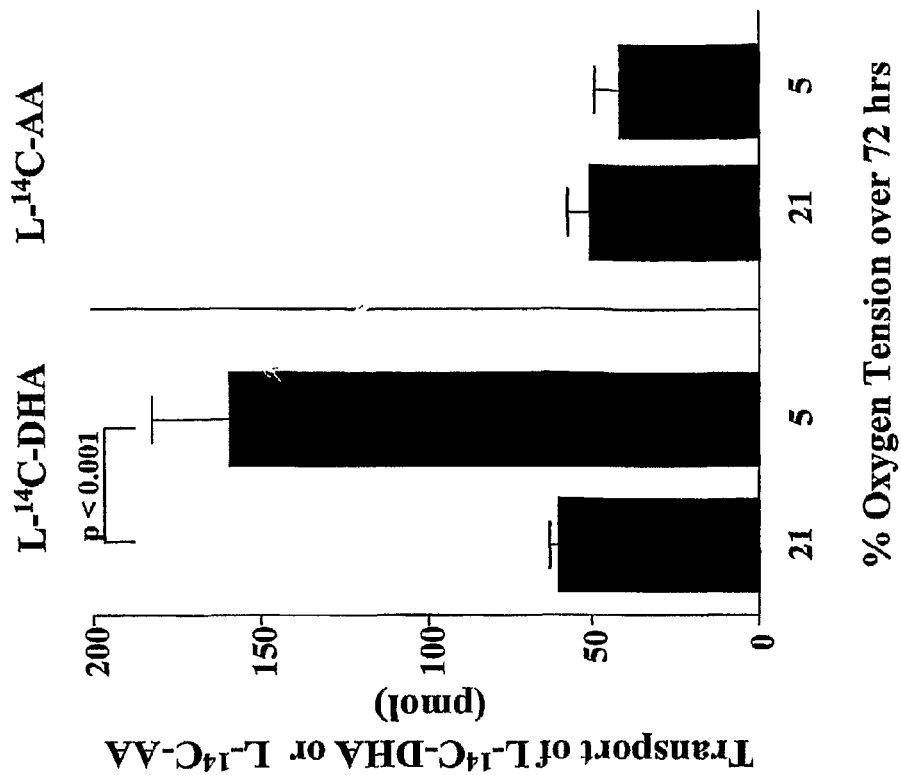
FIG. 11: Upregulation of DHA but not AA Transport under Low Oxygen Tensions. Primary human chondrocytes were incubated in different oxygen tensions for 24 (A) or 72 hours (B). L-$^{14}$C-DHA or L-$^{14}$C-AA transport was measured after 10 minutes at 37° C./5% CO$_2$/21% O$_2$. A. The bars indicate the mean percentage of L-$^{14}$C-DHA transport +/− standard error. The black bars represent the uptake in samples that contain 10 mM D-glucose and the gray bars represent the uptake in samples in the absence of D-glucose. *p<0.001 compared to the corresponding sample in the absence of glucose. $^{\#}$ p<0.001 compared to the corresponding sample at 21% oxygen tension. B. The bars indicate the mean pmol of L-$^{14}$C-DHA/4.5×10$^5$ cells (left panel) or L-$^{14}$C-AA/4.5×10$^5$ cells (right panel) +/− standard error. p<0.001 when comparing AA transport at 5% oxygen tension to DHA transport at 5% oxygen tension.
Figure 11A:
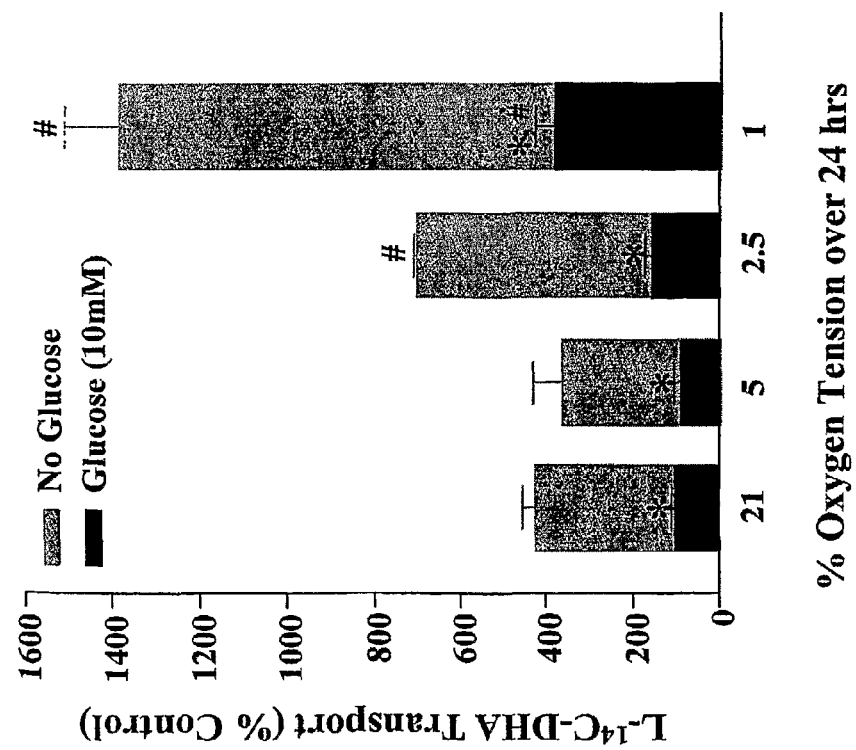

Upregulation of DHA but not AA transport at low oxygen tensions. After 24 hours under 1% oxygen tension, DHA transport into primary human chondrocytes was increased a mean 3.5-fold (FIG. 11A). This was true in both the presence of glucose (3.8-fold, p<0.001) and in the absence of glucose (3.2-fold, p<0.001), as compared to corresponding samples at 21% oxygen tension. However, as expected for transport via the GLUTs, the transport of DHA was significantly inhibited by glucose under all oxygen tensions (p<0.001). A dose response was observed with the greatest increase in L-$^{14}$C-DHA uptake at 1% oxygen (3.5-fold, p<0.001), an intermediate increase at 2.5% oxygen (1.6-fold in the absence of glucose, p<0.001), and no increase at 5% oxygen tension over 24 hours, as compared to 21% oxygen tension.

Exposure to 5% oxygen tension for a longer period of time, 72 hours, lead to a 2.7-fold increase in DHA transport (FIG. 11B, p<0.001), as compared to transport at 21% oxygen tension. On the other hand, there was no change in AA transport at either 1% or 5% oxygen tension (FIG. 11B, data for 5% oxygen after 72 hours is shown). Under physiologic conditions in the joint (in the presence of sodium and glucose at 5% oxygen tension), the amount of DHA transported into primary human chondrocytes was 4-fold greater than the amount of AA transported (p<0.001).

Table 1 provides a summary of the effects of oxygen tension on GLUT1 and GLUT3 mRNA levels, as measured by real time RT-PCR. There were minimal increases in GLUT1 and GLUT3 mRNA levels at 5% oxygen tension after 24 hours, which was consistent with the absence of a measurable change in the uptake of DHA under these conditions. After 24 hours at 1% oxygen tension and after 72 hours at 5% oxygen tension, there were substantial increases in both GLUT1 and GLUT3 mRNA levels and a coincident increase in DHA uptake was also observed.

TABLE 1

Effects of Oxygen Tension on DHA Uptake and GLUT1 and GLUT3 mRNA Levels

| O$_2$ Tension | Time (hrs) | $^{14}$C-DHA Uptake | Fold Change in mRNA Levels* | |
| --- | --- | --- | --- | --- |
| | | | GLUT1 | GLUT3 |
| 1% | 24 | ↑3.8 | +8.6 | +4.3 |
| 5% | 24 | No change | +1.6 | +1.8 |
| 5% | 72 | ↑2.7 | +5.2 | +2.5 |

*The real time RT-PCR data is expressed as the fold change in GLUT1 or GLUT3 mRNA levels under the indicated oxygen tension, as compared to the mRNA levels at 21% oxygen tension. All data were corrected for 18S rRNA levels in each sample.

AA and DHA in patient samples. HPLC analyses of synovial fluid from subjects with knee OA showed that on average, the synovial fluid contained 74 μM AA and 6 μM DHA. The paired plasma samples from these patients contained 49 μM AA and 5 μM DHA. Therefore, the vast majority of Asc in both plasma and synovial fluid was in the form of AA in patients with OA (p<0.001). There was no difference in the proportion of synovial fluid DHA from knees with different levels of OA severity (data not shown). Overall, the synovial fluid contained significantly higher concentrations of AA than the plasma (p<0.001), corresponding to 8% of the total Asc in the form of DHA and 92% as AA (Table 2). By comparison, the previously reported percentages of AA and DHA in the blood of non-arthritic patients, 86% AA and 14% DHA (34), were similar to those measured in OA patients. In contrast, reported values for RA patients were roughly the inverse of those in OA patients, namely 20% AA and 80% DHA, in both synovial fluid and blood (34).

In summary, we provide the first evidence that human chondrocytes transport DHA via the GLUTs and that this transport mechanism in chondrocytes is modestly selective for L-DHA and is a physiologically relevant pathway for increasing intracellular Asc levels. This DHA transport mechanism is expected to be extremely important in RA patients, where the inflammatory environment increases the proportion of DHA in the blood and synovial fluid. By virtue of the upregulation of the DHA pathway in the hypoxic milieu of cartilage, this mechanism of transport is also expected to provide a substantial amount of intracellular Asc to chondrocytes, which is necessary for their function and cartilage extracellular matrix production.

TABLE 2

Percentage of Ascorbic Acid (AA) and Dehydroascorbate (DHA) in Patient Samples

| Patients | Blood | | Synovial Fluid | | Predicted Physiologic Transport Pathways | |
|---|---|---|---|---|---|---|
| | % AA | % DHA | % AA | % DHA | SVCT2 (%) | GLUTs (%) |
| OA n = 23 | 91 | 9 | 92 | 8 | 74 | 26 |
| Non-arthritic* n = 20 | 86 | 14 | ND+ | ND+ | 61 | 39 |
| RA* n = 13 | 19 | 81 | 20 | 80 | 6 | 94 |

*Data from non-arthritic and RA samples is from Lunec and Blake (34).
+ND = not determined

EXAMPLE 4

Proof of Concept Experiments

Figure 12:
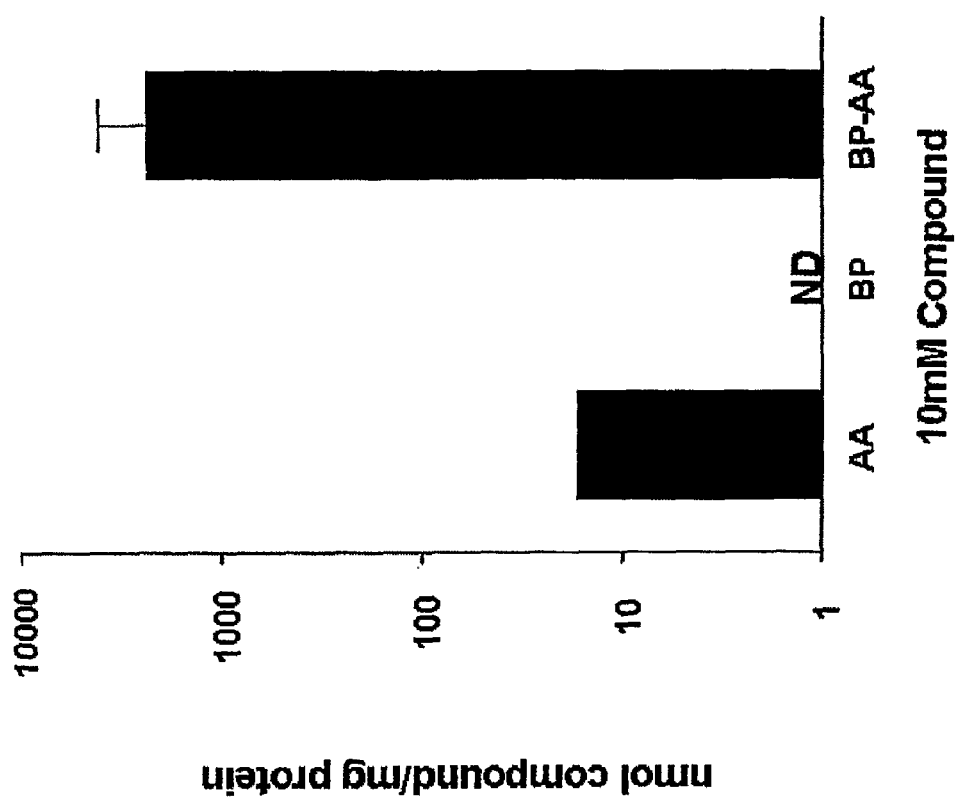
FIG. 12: Bisphosphonate-conjugated to ascorbic acid (BP-AA) is transported into chondrocytes much more efficiently than either the BP or AA alone.

We have determined that 2281 nmol/mg protein bisphosphonate-conjugated to ascorbic acid (BP-AA) is able to gain entry to chondrocytes in monolayer when presented for one hour with 10 mM BP-AA. However, we were unable to detect any free BP inside cells that were simultaneously incubated with 10 mM free BP. In addition, the BP-AA was transported 143-fold more than AA alone. Therefore, the BP-AA conjugate was transported much more efficiently than either the BP or AA alone. (FIG. 12)

Uptake Assay Methods. Primary human chondrocytes were seeded at a density of $4.5 \times 10^5$ cells for 48 hours. The cells were washed with ascorbic acid transport buffer. The free bisphosphonate (BP) and the bisphosphonate conjugated to ascorbic acid (BP-AA) were solubilized in ascorbic acid transport buffer at 10 mM concentration. The cells were incubated with either the free BP or the BP-AA for an hour at 37° C./5% $CO_2$. The cells were washed 4× with ice-cold PBS to remove any extracellular BP or BP-AA. The cells were then lysed in 250 µl dd$H_2O$ for 15 minutes on ice, sonicated for 5 minutes, and then scraped from the culture dish. The lysate was then analyzed by ion pair reverse phase HPLC with UV and electrochemical detection (ECD) as described below.

HPLC Methods. Ascorbic acid, free and conjugated, and risedronate analogs were determined by a modification of an ion pair reverse phase high-performance liquid chromatography method initially described by Vallano et al. (Vallano, P. T., Shugarts, S. B., Kline, W. F., Woolf, E. J., and Matuszewski, B. K., Determination of Risedronate in Human Urine by Column-Switching Ion-Pair High-Performance Liquid Chromatography with Ultraviolet Detection. *J Chromatogr B Analyt Technol Biomed Life Sci*, 2003, 794:23-33). The column consisted of a $C_{18}$ packing, the mobile phase contained 8% acetonitrile and 92% of 0.005M Q8 (1-octyltriethylammonium phosphate [Regis Technologies, Morton Grove, Ill.]) and 1 mM etidronate (1-hydroxyethylidene-1,1-diphosphonic acid [Strem Chemicals, Newburyport, Mass.]) in a sodium phosphate buffer, pH 6.2, and was pumped at mL/min. The injection volume was 100 µl and detection was at 262 nm (UV) and 0.7V (ECD).

Figure 13:
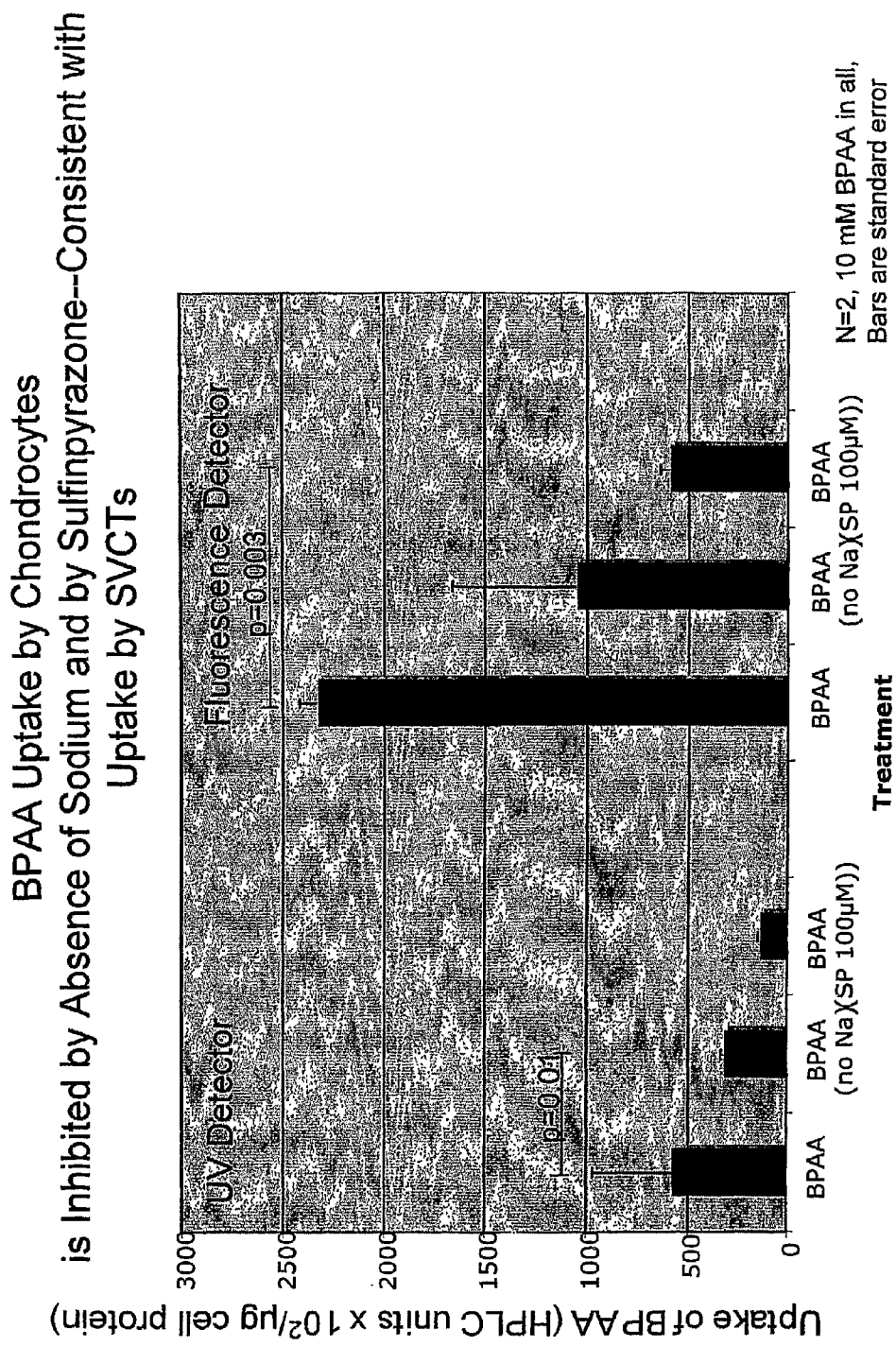
FIG. 13: BPAA uptake by chondrocytes is inhibited by absence of sodium and by sulfinpyrazone—Consistent with uptake by SVCTs.

As shown in FIG. 13, we have confirmed in a separate set of experiments that bisphosphonate-conjugated to ascorbic acid (BP-AA) is able to gain entry into chondrocytes in monolayer when presented for one hour with 10 mM BP-AA. The uptake of BP-AA was inhibited 50% in the absence of sodium. In addition, the uptake of BP-AA was inhibited approximately 75% by 100 µM sulfinpyrazone, an anion transport inhibitor, incubated with chondrocytes in monolayer 45 minutes in advance of the BPAA. Therefore, we demonstrate once again, ability of an ascorbic acid conjugate, namely BP-AA, to gain entry into chondrocytes. The dependence of this transport on sodium, and its inhibition by sulfinpyrazone demonstrates that the uptake of BP-AA is mediated by sodium dependent vitamin C transporters.

The foregoing is illustrative of the present invention, and is not to be construed as limiting thereof. The invention is defined by the following claims, with equivalents of the claims to be included therein.

What is claimed is:

1. A compound of the formula:

$$A^1\text{-}L\text{-}B^1 \text{ or } A^1\text{-}B^1 \tag{I}$$

wherein:
$A^1$ is ascorbic acid, dehydroascorbic acid, ascorbyl-2-phosphate, or their salts or analogs thereof;
L is a linking group coupled to said ascorbic acid, dehydroascorbic acid, ascorbyl-2-phosphate, their salts or analogs at the C5 or C6 position thereof; and
$B^1$ is a bisphosphonate active agent;
or a pharmaceutically acceptable salt thereof;
wherein said bisphosphonate active agent is of Formula (II):

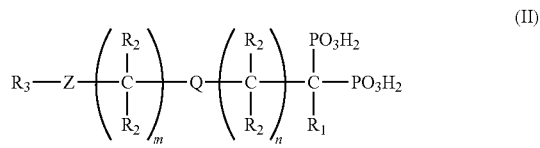

wherein:
Q is oxygen, —$NR_4$—, selenium, —N—, or a single bond;
m+n is an integer from 0 to about 5;
Z is a five or six-membered aromatic ring selected from the group consisting of pyridine, pyridazine, pyrimidine, and pyrazine;
$R_1$ is hydrogen, substituted or unsubstituted amino, amido, hydroxy, alkoxy, halogen, carboxylate, substituted or unsubstituted alkyl having from 1 to 6 carbon atoms, substituted or unsubstituted aryl, or substituted or unsubstituted benzyl, except that when n=0 and Q is oxygen, selenium, or —$NR_4$— then $R_1$ is hydrogen, substituted or unsubstituted alkyl having from 1 to about 6 carbon atoms, substituted or unsubstituted aryl, or substituted or unsubstituted benzyl, with $R_1$ being hydrogen, chloro, amino, methyl, or hydroxy;
each $R_2$ is, independently, hydrogen, or substituted or unsubstituted alkyl having from 1 to 4 carbon atoms;
$R_3$ is one or more substituents selected from the group consisting of hydrogen, substituted or unsubstituted alkyl having from 1 to about 6 carbon atoms, substituted and unsubstituted aryl, substituted and unsubstituted benzyl, hydroxy, halogen, carbonyl, alkoxy, nitro, amido, amino, substituted amino, carboxylate, and combinations thereof;
$R_4$ is hydrogen, substituted or unsubstituted alkyl having from 1 to about 4 carbon atoms, or acyl, and for any of the $R_1$, $R_2$, $R_3$, or $R_4$ substituents which are themselves substituted, the substitution on these substituents may be any one or more of methyl, ethyl, amino, chloro, nitro, methoxy, hydroxy, acetamido, and acetate; and linking group L is coupled either to Z or to a substituent $R_3$.

2. The compound of claim 1, wherein $A^1$ is selected from the group consisting of ascorbic acid, the oxidized derivative, dehydroascorbic acid (DHA), and ascorbyl-2-phosphate (A2P), 6-chloro-6-deoxy-L-ascorbic acid/-A2P, 6-bromo-6-deoxy-L-ascorbic acid/-A2P, 6-deoxy-6-fluoro-L-ascorbic acid/-A2P, 6-deoxy-6-iodo-L-ascorbic acid/-A2P, 5-chloro-5-deoxy-L-ascorbic acid/-DHA/-A2P, 5-bromo-5-deoxy-L-ascorbic acid/-DHA/-A2P, 5-deoxy-5-fluoro-L-ascorbic acid/-DHA/-A2P, 5-deoxy-5-iodo-L-ascorbic acid/-DHA/-A2P.

3. The compound of claim 1, wherein $A^1$ is

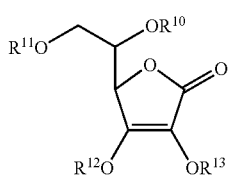

wherein:
one of $R^{10}$ and $R^{11}$ is H and the other is a covalent link to $B^1$ or L; and
$R^{12}$ and $R^{13}$ are each independently selected from the group consisting of H and $PO_3H_2$, subject to the proviso that at least one of $R^{12}$ and $R^{13}$ is $PO_3H_2$.

4. The compound of claim 1, wherein $A^1$ is

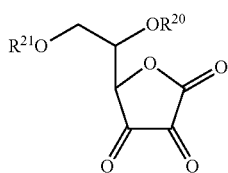

wherein:
one of $R^{20}$ and $R^{21}$ is H and the other is a covalent link to $B^1$ or L.

5. The compound of claim 1, wherein $B^1$ is selected from the group consisting of alendronate, risedronate, tiludronate, ibandronate, zolendronate, pamidronate, etidronate, and salts and esters thereof.

6. The compound of claim 1 having the structure:

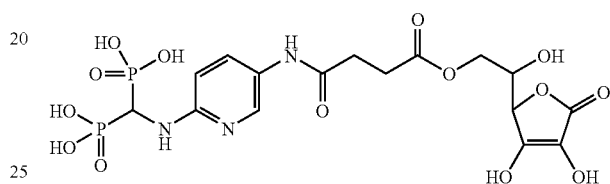

(a)

or a pharmaceutically acceptable salt or prodrug thereof.

7. A composition comprising a compound of claim 1 in a pharmaceutically acceptable carrier.

8. A method of inhibiting bone resorption in a subject in need thereof, comprising administering said subject a treatment-effective amount of a compound of claim 1.

9. A method of treating osteoporosis in a subject in need thereof, comprising administering said subject a treatment-effective amount of a compound of claim 1.

10. The compound of claim 1 having the structure:

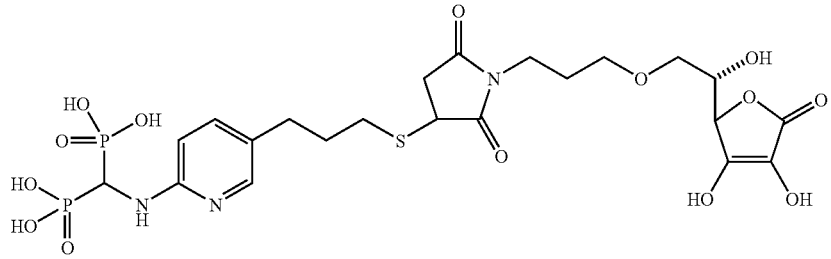

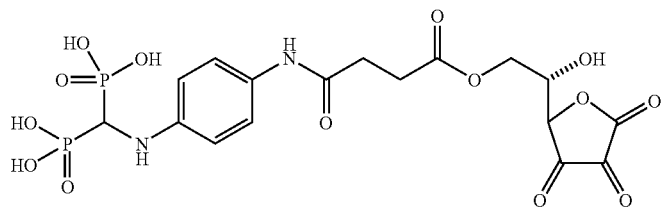

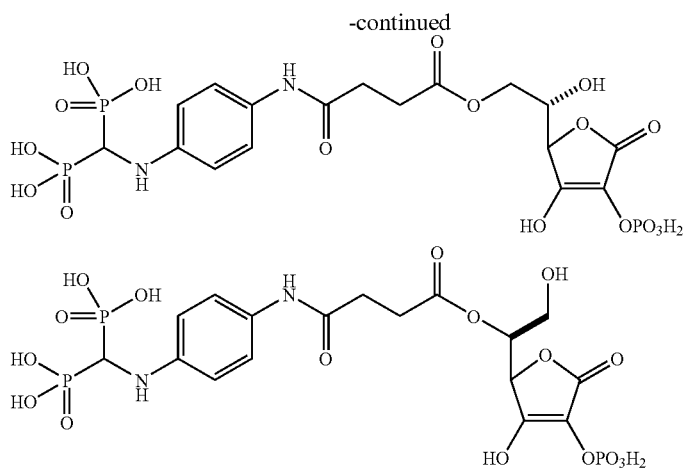

or a pharmaceutically acceptable salt thereof.

11. The compound of claim 1, wherein L is selected from the group consisting of alkylene, alkylenecarbonyl, carbonylalkylene, carbonyl, maleimide, phenyl, ester, and combinations thereof.

12. The compound of claim 1, wherein L is selected from the group consisting of:

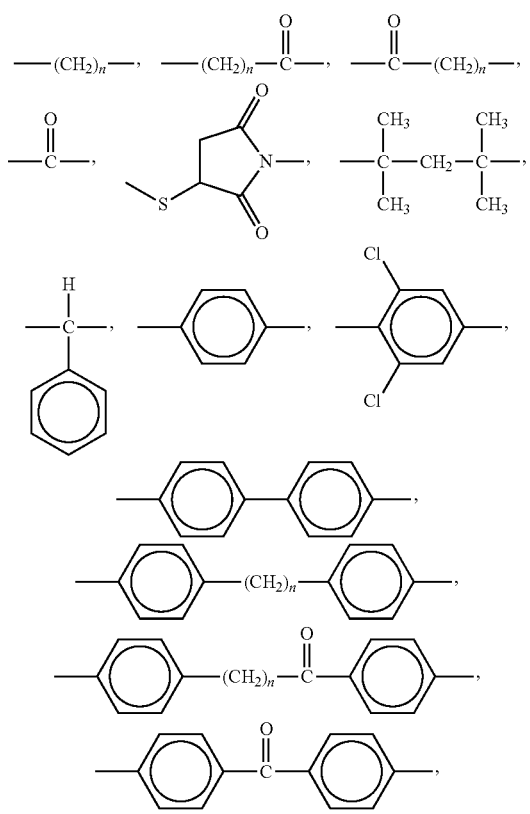

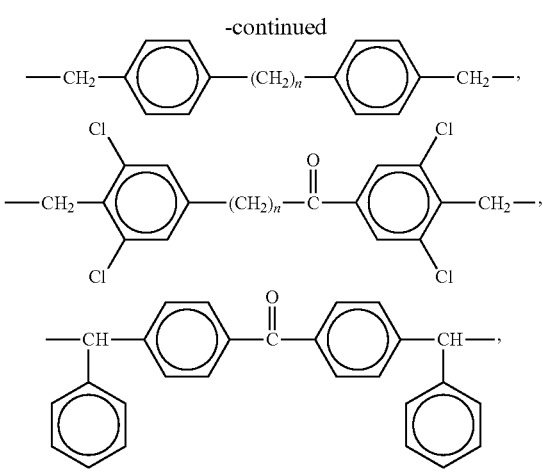

and combinations thereof, optionally further comprising an ester linkage, and where n is 1 to 6.

13. The compound of claim 1 having the structure $A^1$-$B^1$.

14. The compound of claim 11, wherein said bisphosphonate is selected from the group consisting of alendronate, risedronate, tiludronate, ibandronate, zolendronate, pamidronate, etidronate, and pharmaceutically acceptable salts thereof.

15. The compound of claim 12, wherein said bisphosphonate is selected from the group consisting of alendronate, risedronate, tiludronate, ibandronate, zolendronate, pamidronate, etidronate, and pharmaceutically acceptable salts thereof.

16. The compound of claim 13, wherein said bisphosphonate is selected from the group consisting of alendronate, risedronate, tiludronate, ibandronate, zolendronate, pamidronate, etidronate, and pharmaceutically acceptable salts thereof.

* * * * *

UNITED STATES PATENT AND TRADEMARK OFFICE
CERTIFICATE OF CORRECTION

PATENT NO.       : 8,247,572 B2
APPLICATION NO.  : 11/911679
DATED            : August 21, 2012
INVENTOR(S)      : Kraus et al.

It is certified that error appears in the above-identified patent and that said Letters Patent is hereby corrected as shown below:

In the Claims:

Column 31, Claim 2, Line 7:   Please correct "wherein $A^l$ is" to read -- wherein $A^1$ is --

Column 31, Claim 3, Line 17: Please correct "wherein $A^l$ is" to read -- wherein $A^1$ is --

Signed and Sealed this
Fourth Day of June, 2013

Teresa Stanek Rea
*Acting Director of the United States Patent and Trademark Office*